United States Patent
Mesilaty-Gross et al.

(10) Patent No.: US 9,103,836 B2
(45) Date of Patent: Aug. 11, 2015

(54) PROCOLLAGEN C-PROTEINASE ENHANCER (PCPE) BIOMARKER FOR BONE FORMATION

(75) Inventors: Shlomit Mesilaty-Gross, Kochav Yair (IL); Yair Anikster, Jerusalem (IL); Ido Wolf, Or-Yehuda (IL)

(73) Assignee: TEL HASHOMER MEDICAL RESEARCH INFRASTRUCTURE AND SERVICES LTD, Ramat Gan (IL)

( * ) Notice: Subject to any disclaimer, the term of this patent is extended or adjusted under 35 U.S.C. 154(b) by 1211 days.

(21) Appl. No.: 12/936,035

(22) PCT Filed: Apr. 1, 2009

(86) PCT No.: PCT/IB2009/051376
§ 371 (c)(1),
(2), (4) Date: Feb. 23, 2011

(87) PCT Pub. No.: WO2009/122367
PCT Pub. Date: Oct. 8, 2009

(65) Prior Publication Data
US 2011/0143371 A1    Jun. 16, 2011

Related U.S. Application Data

(60) Provisional application No. 61/064,901, filed on Apr. 2, 2008.

(51) Int. Cl.
G01N 31/00 (2006.01)
G01N 33/53 (2006.01)
G01N 33/68 (2006.01)

(52) U.S. Cl.
CPC ........ *G01N 33/6893* (2013.01); *G01N 2333/78* (2013.01); *G01N 2800/10* (2013.01)

(58) Field of Classification Search
CPC ... C07K 14/56; A61K 38/212; A61K 9/0019; C12Q 1/6858
See application file for complete search history.

(56) References Cited

U.S. PATENT DOCUMENTS

| 4,857,456 A | 8/1989 | Urist |
| 6,037,139 A | 3/2000 | Greenspan et al. |
| 6,803,453 B1 | 10/2004 | Brunkow et al. |
| 8,518,656 B2 * | 8/2013 | Mesilaty-Gross et al. ... 435/7.21 |
| 2003/0224501 A1 | 12/2003 | Young et al. |

FOREIGN PATENT DOCUMENTS

| JP | 1095797 | 4/1998 |
| WO | 2002068962 A2 | 9/2002 |

OTHER PUBLICATIONS

Yang L, Grey V. Pediatric reference intervals for bone markers. Clin Biochem. 2006 39(6):561-8.
Seibel MJ. Biochemical markers of bone turnover: part I: biochemistry and variability. Clin Biochem Rev. 2005 26 (4):97-122.
Gelse K, Poschl E, Aigner T. Collagens—structure, function, and biosynthesis. Adv Drug Deliv Rev. 2003 55 (12):1531-46.
Voorzanger-Rousselot N, Garnero P. Biochemical markers in oncology. Part I: molecular basis. Part II: clinical uses. Cancer Treat Rev. 2007 33: 230-283.
Barry M. Steiglitz et al."Procollagen C Proteinase Enhancer 1 Genes are Important Determinants of the Mechanical Properties and Geometry of Bone and the Ultrastructure of Connective Tissues" Molecular and Cellular Biology. Jun. 2006, p. 238-249.

* cited by examiner

*Primary Examiner* — Lisa Cook
(74) *Attorney, Agent, or Firm* — Browdy and Neimark, PLLC

(57) ABSTRACT

A method of analyzing bone formation or determination of cell state with regard to differentiation of osteoblasts and/or fibroblasts in a subject is provided, the method comprising detecting PCPE isoforms in a biological sample from the subject; and comparing the PCPE isoforms from the sample of biological fluid with PCPE isoforms of a predetermined standard or a sample obtained from healthy individuals.

13 Claims, 17 Drawing Sheets

Figure 1A

Q15113 Procollagen C-endopeptidase enhancer 1, Homo sapiens (Human)

```
         10         20         30         40         50         60
                                      ↓
                              QTPNY TRPVFLCGGD
                                        ↓

70         80         90        100        110        120
                                                           LGR  FCGTFRFAPL 130        140        150        160        170        180
                              ↓
VAPGNQVTLR                  GPLLRYVQRA                 QRLEKAQGTL TIFNWPESDY 190        200        210        220        230        240
PPGISCSWHI IAPPIQVIAL TFEEFDLEPD TYCRYDSVSV PGGNISDSK RLGKFCGDAV 250        260        270        280        290        300
PGSISSEGNE LLVQFVSDLS VTADGFSASY KTLPRGTAKE GQGPCPKRGT EPKVKLPPKS 310        320        330        340        350        360
                                    QCRRTGTLQS                  GEGLAVTVSL 370        380        390        400        410        420
IGAYKTGGLD LPSPPTGASL KFYVPCKQCP PMKK                      GP VLPPESFVVL 430        440
HRPNQDQILT NLSKRK          AAASQD
```

↓ CUB1  ‡ CUB2  ⁑ NTR
  Signal peptide
* Trypsin peptides
* Potential N glycosylation site Figure 1B
```
Peptides:
     43 GESGYVASEGFPNLYPPNK
     81 VFDLELHPACR
     92 YDALEVFAGSGTSGQR
    131 MTTDEGTGGR
    141 GFLLWYSGR
    150 ATSGTEHQFCGGR
    205 FDLEPDTYCR
    215 YDSVSVFNGAVSDDSR
    215 YDSVSVFNGAVSDDSRR
    300 SQPPEKTEESPSAPDAPTCPK
    306 TEESPSAPDAPTCPK
    325 TGTLQSNFCASSLVVTATVK
    366 TGGLDLPSPPTGASLK
    395 GVSYLLMGQVEENR
    436 KCPSQPVR
```

Interpretation table
N-Linked
  Bi Antennary          High
  Tri/Tetra
  Antennary             Not Detected
  High Mannose          Not Detected
  Sialic Acid           Low
  Terminal
  GlcNAc                Low
  Terminal
  GalNAc                Not Detected
  Bisecting
  GlcNAc                Not Detected
O-Glycans               Not Detected

PROCOLLAGEN C-PROTEINASE ENHANCER (PCPE) BIOMARKER FOR BONE FORMATION

CROSS REFERENCE TO RELATED APPLICATION

The present application is a 35 U.S.C. §371 National Phase application of International Application Ser. No. PCT/IB2009/51376, filed Apr. 1, 2009, which claims priority to U.S. Provisional Application 61/064,901, filed April 2, 2008. The disclosures of both applications are incorporated herein by reference in their entirety.

FIELD OF THE INVENTION

The present invention relates to the field of diagnostics, and more particularly, to use of procollagen C-proteinase enhancer (PCPE) as a biomarker for bone formation.

BACKGROUND OF THE INVENTION

Normal bone is constantly being remodeled, or broken down and rebuilt.

Every week, humans recycle 5% to 7% of their bone mass. This remodeling process serves two primary functions: maintaining blood calcium levels and keeping the skeleton strong.

Two types of cells are involved in the remodeling of bone: osteoclasts and osteoblasts. Osteoclasts are the cells that break down bone, converting the calcium salts to a soluble form that passes easily into the blood. Osteoblasts produce the organic fibers on which calcium salts are deposited. In healthy young adults, the activities of these two cell types are balanced so that total bone mass remains constant.

Remodeling is a cyclic process that occurs at specific skeletal sites, with each remodeling cycle lasting about four months. Since bone resorption occurs rather quickly, most of the cycle is devoted to bone formation. The major event that triggers bone formation is the transition of mesenchymal stem cells into osteoblast cells. Osteoblasts deposit extracellular matrix (ECM) proteins to form the bone scaffold which subsequently mineralize[1].

The collagens that form fibrils are the most abundant components of most connective tissue and provide the three-dimensional scaffold that maintains tissue integrity[2-4]. Collagen type I is the major ECM protein of the bone, comprising 90% of its organic mass, and is highly expressed during bone formation[5].

Collagen type I and other filbrillar collagens are first synthesized and secreted into the ECM in the form of soluble precursor, procollagen[6]. Proteolytic processing of procollagen N-propeptide and C-propeptide (PINP and PICP, respectively) by specific N- and C-proteinase lead to the production of mature collagen monomer capable of forming fibrils. PICP is cleaved by bone morphogenetic protein-1 (BMP-1)[7]. BMP-1 is a multi substrate enzyme, among its substrates are procollagen type I, II, III and other ECM precursors, such as lysyl oxidase, laminin 5, chordin, and pro-biglycan[8,9]. The cleavage of PICP by BMP-1 lowers procollagen solubility by at least a thousand fold and is critical for the self-assembly of collagen fibrils[10]. The rate of this processing appears to control fibril formation[11]. BMP-1 C-propeptide processing activity is regulated by another component of the ECM, PCPE[12, 13].

In their search for bone formation markers, researchers have focused on metabolites and enzymes specific to osteoblast activity, mainly those involved in collagen type I synthesis and mineralization, but each was found to have disadvantages[14, 15].

Current markers of bone formation include, among others, circulating procollagen type I C-propeptide (PICP), osteocalcin (OC), and bone-specific alkaline phosphatase (bone ALP). All of these reflect osteoblast activity during the process of bone formation and can be measured in serum[15].

PICP is a soluble trimeric globular protein, produced simultaneously with the production of mature type I collagen molecules from procollagen, and released into the blood[16]. From the blood it is cleared by liver endothelial cells via the mannose receptor and has a short serum half life of 6-8 min. PICP may arise from other sources like tendons, skin, ligaments, cornea, and many interstitial connective tissues, but these non-skeletal tissues exhibit a slower turnover than bone, and contribute very little to the circulating propeptide pool. Different studies have shown good correlation between serum PICP levels and rate of bone formation but its clinical relevance is still viewed with skepticism[17].

Osteocalcin is the most abundant non-collagenous protein of bone matrix. As opposed to PICP, osteocalcin is exclusively present in bone tissue, increasing significantly when skeletal growth is boosted. However its serum concentration has circadian variations, it is relatively unstable in serum samples and considerable inconsistencies have been reported among laboratories[14]. Other disadvantages include its release during bone resorption and rapid clearance by the kidney. In breast cancer patients with bone metastases, serum OC lacks diagnostic sensitivity compared to bone ALP, but in multiple myeloma patients, low levels of OC were found to be associated with severity of the disease and survival[17].

Bone alkaline phosphatase (bone ALP) is an enzyme localized in the membrane of osteoblasts that is released into the circulation. The liver and the bone isoenzymes are the major contributors to the serum level of total ALP. Serum total ALP activity is the most commonly used marker of bone formation but it lacks specificity. Although most of the methods used to monitor the level of bone ALP have proved to be insensitive, nonspecific (as there was cross-reactivity with liver ALP) or technically complicated, in prostate cancer, bone ALP has been shown to be a more sensitive indicator than total ALP in the detection of bone metastases[17]. The precise function of the enzyme is yet unknown but it obviously plays an important role in osteoid formation and mineralization[15].

U.S. Pat. No. 4,857,456 discloses an assay of BMP and anti-BMP antibody for the diagnosis of bone disorders, which may be carried out by comparing the BMP, anti-BMP antibody, or the ratio of the two to normal assay standards.

U.S. 2003224501 discloses use of BMP polynucleotides, polypeptides, and antibodies for diagnostic use.

U.S. Pat. No. 6,037,139 teaches a system for assaying modulators of procollagen maturation, but does not teach the use of such modulators as biological markers.

U.S. Pat. No. 6,803,453 teaches use of antibodies associated with alterations in bone density. The compositions are useful in the diagnosis, prevention and/or treatment of diseases associated with a loss of bone density, such as osteoporosis.

WO 02/068962 teaches methods for determining cartilage degeneration or regeneration in a joint tissue in a patient by measuring levels of osteogenic protein-1 OP-1 or BMP7) protein and/or mRNA in synovial fluid or joint tissue.

The background art teaches proteins related to BMP. However, BMP1 is an enzyme, while the remaining BMP proteins are not enzymes and have completely different roles. BMP1 is active post modelling for specific collagen deposition, while the others operate earlier in the process and affect bone cell activities. They are also related to non-bone activities, particularly BMP 1. However, none of them are accurate, specific biochemical markers for bone formation which are sufficiently accurate and specific to be used as a single marker.

Bone morphogenetic proteins (BMPs) were first identified in fraction of demineralized bone extracts, and named for their ability to induce ectopic andochondral bone formation when implanted into the soft tissues of rodents[18]. BMP1 differed from the other BMPs members which are all members of the transforming growth factor (TGF)-β superfamily of growth factors, in possessing a distinct protein domain structure, that included a conserved protease domain. To date, at least 20 BMPs have been identified, some of which have been shown in vitro to stimulate the process of stem cell differentiation into osteoblasts in human and animal models. Having realized the osteoinductive properties of BMPs and having identified their genetic sequences, recombinant gene technology has been used to produce BMPs for clinical application—most commonly, as alternatives or adjuncts in the treatment of cases in which fracture healing is compromised. BMP-2 and BMP-7 are approved for clinical use in open fractures of long bones, non-unions and spinal fusion. However, despite significant evidence of their potential benefit to bone repair and regeneration in animal and preclinical studies, there is, to date, a dearth of convincing clinical trials[19].

SUMMARY OF THE INVENTION

The background art does not teach or suggest a biochemical marker that provides accurate assessment of bone formation, and is devoid of at least some of the limitations of the prior art.

The present invention overcomes these drawbacks of the background art by providing a method, marker and kit for analysis of bone formation using procollagen C-proteinase enhancer (PCPE), a protein that enhances the synthesis of collagen type I, II and III, as a marker.

The term "PCPE" optionally and preferably refers to a protein that is also known as "Procollagen C-endopeptidase enhancer 1" or "PCPE-1", with SwissProt identifier PCOC1_HUMAN (primary accession number Q15113). The sequence of this protein is given below:

MLPAATASLLGPLLTACALLPFAQGQTPNYTRPVFLCGGDVKGESGYVA

SEGFPNLYPPNKECIWTITVPEGQTVSLSFRVFDLELHPACRYDALEVF

AGSGTSGQRLGRFCGTFRPAPLVAPGNQVTLRMTTDEGTGGRGFLLWYS

GRATSGTEHQFCGGRLEKAQGTLTTPNWPESDYPPGISCSWHIIAPPDQ

VIALTFEKFDLEPDTYCRYDSVSVFNGAVSDDSRRLGKFCGDAVPGSIS

SEGNELLVQFVSDLSVTADGFSASYKTLPRGTAKEGQGPGPKRGTEPKV

KLPPKSQPPEKTEESPSAPDAPTCPKQCRRTGTLQSNFCASSLVVTATV

KSMVREPGEGLAVTVSLIGAYKTGGLDLPSPPTGASLKFYVPCKQCPPM

KKGVSYLLMGQVEENRGPVLPPESFVVLHRPNQDQILTNLSKRKCPSQP

VRAAASQD

The data presented herein relate at least primarily to PCPE-1; however other forms of PCPE, such as PCPE-2, are not excluded from being encompassed within the present invention.

According to some embodiments of the present invention, there is provided a use of procollagen C-proteinase enhancer (PCPE), preferably PCPE-1, as a marker of bone formation.

According to other embodiments of the present invention, there is provided a method of analyzing bone formation in a subject, the method comprising: detecting a PCPE pattern in a biological sample from the subject; and comparing the PCPE pattern from the sample of biological fluid with a PCPE pattern of a predetermined standard, wherein PCPE is preferably PCPE-1. The method preferably further comprises separating proteins of the biological sample. Optionally, the separating comprises a technique selected from the group consisting of electrophoresis separation and chromatography separation. Optionally, the electrophoresis separation comprises one or more of SDS-polyacrylamide gel electrophoresis (SDS-PAGE), isoelectrofocusing (IEF) and 2 dimensional electrophoresis (2DE). Optionally, the chromatography separation comprises one or more of gel filtration, adsorption, ion exchange, and affinity separation.

According to some embodiments, the detecting comprises detecting PCPE with mass spectroscopy, for example LC-MS/MS (liquid chromatography combined with mass spectroscopy for direct detection of the component peptides).

Preferably, the detecting comprises: contacting the biological sample with labeled anti-PCPE antibody to form a PCPE/anti-PCPE antibody complex; and detecting the complex.

Optionally and if anti-PCPE is not labeled, the detecting the complex comprises contacting the anti-PCPE antibody with secondary antibody conjugated to enzyme (ALK, HRP, fluorescence or any other labeling). Also optionally, the detecting the complex comprises visualization by one or more of colorimetric methods and electrochemiluminescence (ECL).

Preferably, the biological sample is selected from the group consisting of serum, plasma, urine, cerebrospinal fluid and cell extract or cell medium.

Optionally, the method is used for one or more of diagnosis of growth disorders, diagnosis of aging, diagnosis of organ fibrosis, diagnosis of osteoporosis, diagnosis of cancer metastasis, and diagnosis one or more of the following diseases: Paget's disease, Osteomalacia, Rickets, bone tumors, osteoporosis, bone changes occurring due to parathyroid disorders and the like. Optionally and preferably, PCPE may be used to diagnose metastasis of cancer cells to bone or out of bone (ie metastasis of a bone related cancer from a primary site in bone tissue to one or more other locations in the body). Non-limiting examples of data from actual patients with breast or prostate cancer demonstrates that PCPE is a useful biomarker that can differentiate between patients with or without bone metastasis or metastases.

According to still other embodiments of the present invention, there is provided a kit for analysis of bone formation, the kit comprising a reagent for purification and detection of PCPE, wherein PCPE preferably comprises PCPE-1. However, without wishing to be limited, the experimental results below relate to PCPE-1 (according to both sequence data from MS and also according to specific binding by an antibody specific to PCPE-1, as described in greater detail below).

Preferably, the reagent comprises an antibody against PCPE. Optionally the kit further comprises an Elisa plate and/or an affinity purification column. Optionally, the kit further comprises at least one reagent selected from the group consisting of a buffer, an antibody and a colorimetric reagent.

Optionally, the kit further comprises a western blot substrate and an antibody.

As used herein the phrase "disease" includes any type of pathology and/or damage, including both chronic and acute damage, as well as a progress from acute to chronic damage.

The term "marker" in the context of the present invention refers to a peptide, or a polypeptide, which is differentially present in a sample taken from patients (subjects) having one of the herein-described diseases or conditions, as compared to a comparable sample taken from subjects who do not have one the above-described diseases or conditions.

The phrase "differentially present" refers to differences in the quantity and/or one or more characteristics (such as glycosylation or ubiquination, or other posttranslational modification) of a marker present in a sample taken from patients having one of the herein-described diseases or conditions as compared to a comparable sample taken from patients who do not have one of the herein-described diseases or conditions. The characteristic may optionally also relate to a pattern exhibited by PCPE, for example due to different glycosylation and/or fragmentation of PCPE from a 50 kd protein to two subunits, 30 kd and 20 kd respectively. For example, it is possible a polypeptide is differentially present between the two samples if the amount of the polypeptide in one sample is significantly different from the amount of the polypeptide in the other sample. It should be noted that if the marker is detectable in one sample and not detectable in the other, then such a marker can be considered to be differentially present. Optionally, a relatively low amount of up-regulation may serve as the marker, as described herein. One of ordinary skill in the art could easily determine such relative levels of the markers; further guidance is provided in the description of PCPE below.

As another example (and also as shown below), the pattern of PCPE may change, due any change in one or more isoforms, optionally featuring the addition or removal of any particular isoform. Non-limiting examples of such changes include changes to the glycosylation pattern and/or fragmentation pattern and/or some other pattern. The glycosylation pattern may optionally be affected by the amount, number, type and/or location of various saccharides. Any other type of posttranslational modification may also optionally change, including with regard to addition, removal or alteration. There may optionally be changes involving combinations with one or more other proteins or materials, for example with regard to ubiquination, or any other covalent change to PCPE or a portion thereof.

As used herein the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above.

Diagnosis of a disease according to the present invention can be effected by determining a level of PCPE in a biological sample obtained from the subject, wherein the level determined can be correlated with predisposition to, or presence or absence of the disease. It should be noted that a "biological sample obtained from the subject" may also optionally comprise a sample that has not been physically removed from the subject.

As used herein, the term "level" refers to the amount of PCPE present. Typically the level of the marker in a biological sample obtained from the subject is different (i.e., increased or decreased) from the level of the same variant in a similar sample obtained from a healthy individual (examples of biological samples are described herein).

Numerous well known tissue or fluid collection methods can be utilized to collect the biological sample from the subject in order to determine the level of PCPE in the subject. Examples include, but are not limited to, fine needle biopsy, needle biopsy, core needle biopsy and surgical biopsy (e.g., brain biopsy), and lavage. Regardless of the procedure employed, once a biopsy/sample is obtained the level of the variant can be determined and a diagnosis can thus be made. Determining the level of the same variant in normal tissues of the same origin is preferably effected along-side to detect an elevated expression and/or amplification and/or a decreased expression, of the variant as opposed to the normal tissues.

A "test amount" of a marker refers to an amount of a marker in a subject's sample that is consistent with a diagnosis of a particular disease or condition. A test amount can be either in absolute amount (e.g., microgram/ml) or a relative amount (e.g., relative intensity of signals). A "control amount" of a marker can be any amount or a range of amounts to be compared against a test amount of a marker. For example, a control amount of a marker can be the amount of a marker in a patient with a particular disease or condition or a person without such a disease or condition. A control amount can be either in absolute amount (e.g., microgram/ml) or a relative amount (e.g., relative intensity of signals).

"Detect" refers to identifying the presence, absence or amount of the object to be detected.

A "label" includes any moiety or item detectable by spectroscopic, photochemical, biochemical, immunochemical, or chemical means. For example, useful labels include 32P, 35S, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The label often generates a measurable signal, such as a radioactive, chromogenic, or fluorescent signal, that can be used to quantify the amount of bound label in a sample. The label may be directly or indirectly detectable. Indirect detection can involve the binding of a second label to the first label, directly or indirectly. Quantitation of the signal is achieved by, e.g., scintillation counting, densitometry, or flow cytometry.

Exemplary detectable labels, optionally and preferably for use with immunoassays, include but are not limited to magnetic beads, fluorescent dyes, radiolabels, enzymes (e.g., horse radish peroxide, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture. "Immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide (or other epitope), refers to a binding reaction that is determinative of the presence of the protein in a heterogeneous population of proteins and other biologies. Thus, under designated immunoassay conditions, the specified antibodies bind to a particular protein at least two times greater than the background (non-specific signal) and do not substantially bind in a significant amount to other proteins present in the sample. Specific binding to an antibody under such conditions may require an antibody that is selected for its specificity for a particular protein. For example, polyclonal antibodies raised to seminal basic protein from specific species such as rat, mouse, or human can be selected to obtain only those polyclonal antibodies that are specifically immunoreactive with seminal basic protein and not with other proteins, except for polymorphic variants and alleles of seminal basic protein. This selection may be achieved by subtracting out antibodies that cross-react with seminal basic protein molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

Antibodies

"Antibody" refers to a polypeptide ligand that is preferably substantially encoded by an immunoglobulin gene or immunoglobulin genes, or fragments thereof, which specifically binds and recognizes an epitope (e.g., an antigen) with regard to PCPE for example. The recognized immunoglobulin genes include the kappa and lambda light chain constant region genes, the alpha, gamma, delta, epsilon and mu heavy chain constant region genes, and the myriad-immunoglobulin variable region genes. Antibodies exist, e.g., as intact immunoglobulins or as a number of well characterized fragments produced by digestion with various peptidases. This includes, e.g., Fab1 and F(ab)!2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

The functional fragments of antibodies, such as Fab, F(ab')2, and Fv that are capable of binding to macrophages, are described as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5 S Fab 1 monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. Fv fragments comprise an association of VH and VL chains. This association may be noncovalent, as described in Inbar et al. [Proc. Nat'l Acad. Sci. USA 69:2659-62 (1972O]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab') or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. MoI. Biol., 227:381 (1991); Marks et al., J. MoI. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Preferably, the antibody of this aspect of the present invention specifically binds at least one epitope of PCPE as described herein. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics. Optionally, a unique epitope may be created in a variant due to a change in one or more post-translational modifications, including but not limited to glycosylation and/or phosphorylation, as described below. Such a change may also cause a new epitope to be created, for example through removal of glycosylation at a particular site. An epitope according to the present invention may also optionally comprise part or all of a unique sequence portion of a variant according to the present invention in combination with at least one other portion of the variant which is not contiguous to the unique sequence portion in the linear polypeptide itself, yet which are able to form an epitope in combination. One or more unique sequence portions may optionally combine with one or more other non-contiguous portions of the variant (including a portion which may have high homology to a portion of the known protein) to form an epitope.

Immunoassays

In another embodiment of the present invention, an immunoassay can be used to qualitatively or quantitatively detect and analyze PCPE as a marker in a sample. This method comprises: providing an antibody that specifically binds to a marker; contacting a sample with the antibody; and detecting the presence of a complex of the antibody bound to the marker in the sample.

To prepare an antibody that specifically binds to a marker, purified protein markers can be used. Antibodies that specifically bind to a protein marker, such as PCPE, can be prepared using any suitable methods known in the art.

After the antibody is provided, a marker can be detected and/or quantified using any of a number of well recognized immunological binding assays. Useful assays include, for example, an enzyme immune assay (EIA) such as enzyme-linked immunosorbent assay (ELISA), a radioimmune assay (RIA), a Western blot assay, or a slot blot assay see, e.g., U.S. Pat. Nos. 4,366,241; 4,376,110; 4,517,288; and 4,837,168). Generally, a sample obtained from a subject can be contacted with the antibody that specifically binds the marker.

Optionally, the antibody can be fixed to a solid support to facilitate washing and subsequent isolation of the complex, prior to contacting the antibody with a sample. Examples of solid supports include but are not limited to glass or plastic in the form of, e.g., a microtiter plate, a stick, a bead, or a microbead. Antibodies can also be attached to a solid support. After incubating the sample with antibodies, the mixture is washed and the antibody-marker complex formed can be detected. This can be accomplished by incubating the washed mixture with a detection reagent. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

The immunoassay can be used to determine a test amount of a marker (PCPE) in a sample from a subject. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can optionally be determined by comparing to a standard. As noted above, the test amount of marker need not be measured in absolute units, as long as the unit of measurement can be compared to a control amount and/or signal.

Preferably used are antibodies which specifically interact with PCPE. Preferred embodiments of antibodies according to the present invention are described in greater detail with regard to the section entitled "Antibodies".

Radioimmunoassay (RIA)

In one version, this method involves precipitation of the desired substrate and in the methods detailed hereinbelow, with a specific antibody and 125 I radiolabeled antibody binding protein (e.g., protein A labeled with radioactive iodine) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme Linked Immunosorbent Assay (ELISA)

This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis. Immunohistochemical analysis: This method involves detection of a substrate in situ in fixed cells by substrate specific antibodies. The substrate specific antibodies may be enzyme linked or linked to fluorophores.

Detection is by microscopy and subjective evaluation. If enzyme linked antibodies are employed, a colorimetric reaction may be required.

Fluorescence Activated Cell Sorting (FACS)

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Radio-imaging Methods

These methods include but are not limited to, positron emission tomography (PET) single photon emission computed tomography (SPECT). Both of these techniques are non-invasive, and can be used to detect and/or measure a wide variety of tissue events and/or functions, such as detecting cancerous cells for example. Unlike PET, SPECT can optionally be used with two labels simultaneously. SPECT has some other advantages as well, for example with regard to cost and the types of labels that can be used. For example, U.S. Pat. No. 6,696,686 describes the use of SPECT for detection of breast cancer, and is hereby incorporated by reference as if fully set forth herein.

Display Libraries

According to still another aspect of the present invention there is provided a display library comprising a plurality of display vehicles (such as phages, viruses or bacteria) each displaying at least 6, at least 7, at least 8, at least 9, at least 10, 10-15, 12-17, 15-20, 15-30 or 20-50 consecutive amino acids derived from PCPE. Methods of constructing such display libraries are well known in the art. Such methods are described in, for example, Young A C, et al., "The three-dimensional structures of a polysaccharide binding antibody to *Cryptococcus neoformans* and its complex with a peptide from a phage display library: implications for the identification of peptide mimotopes" J Mol Biol 1997 Dec. 12; 274(4): 622-34; Giebel L B et al. "Screening of cyclic peptide phage libraries identifies ligands that bind streptavidin with high affinities" Biochemistry 1995 Nov. 28; 34(47): 15430-5; Davies E L et al., "Selection of specific phage-display antibodies using libraries derived from chicken immunoglobulin genes" J Immunol Methods 1995 Oct. 12; 186(1):125-35; Jones C RT al. "Current trends in molecular recognition and bioseparation" J Chromatogr A 1995 Jul. 14; 707(1):3-22; Deng S J et al. "Basis for selection of improved carbohydrate-binding single-chain antibodies from synthetic gene libraries" Proc Natl Acad Sci U S A 1995 May 23; 92(11):4992-6; and Deng S J et al. "Selection of antibody single-chain variable fragments with improved carbohydrate binding by phage display" J Biol Chem 1994 Apr. 1; 269(13):9533-8, which are incorporated herein by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1E show analysis of human PCPE;

DESCRIPTION OF THE PREFERRED EMBODIMENTS

Figures 1C, 1D:
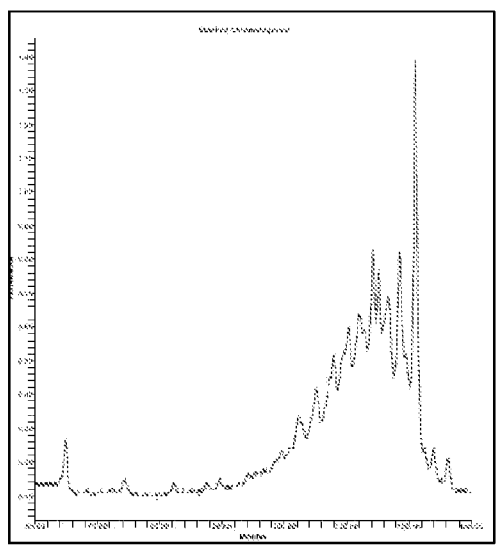

The present invention is of a method for analysis of bone formation using procollagen C-proteinase enhancer (PCPE), a protein that enhances the synthesis of collagen type I, II and III, as a marker.

PCPE is a highly conserved ECM glycoprotein devoid of intrinsic enzymatic activity. It binds to the PICP and increases the activity of BMP-1 on procollagen I by up to tenfold[12,13]. PCPE consists of two N-terminal CUB (Complement 1 q, Urchin, and BMP 1) domains, which are essential for its enhancement activity and procollagen binding[20] and a C-terminal netrin-like (NTR) domain, which induces a weak inhibition of matrix metalloproteinase (MMP)[21]. PCPE enhances procollagen type I and II C-propeptide processing[22] and binds to mini-type III[23]. No such enhancement activity was associated with the non filbrillar substrates of BMP-1. On the basis of these findings Moali[23] suggested that PCPE defines a new class of ECM enzyme adaptors that regulate fibrillar procollagen C-terminal processing activity of BMP-1. PCPE undergoes multiple post-translation modifications as it contains an N-linked oligosaccharide decorated with sialyl residues.[22]

The present inventors have surprisingly found that PCPE serves as an accurate, consistent and sensitive marker of bone formation.

The present invention thus provides a method of analyzing bone formation in a subject, using PCPE as a marker. The method comprises obtaining a PCPE pattern, from a biological sample and comparing the pattern to that of a reference sample.

The present invention further provides a kit for analysis of bone formation in a biological sample, comprising reagents for detection of PCPE. The kit may comprise, for example, anti-PCPE antibody (optionally with label and/or conjugated marker and/or any other marker). Optionally, the kit comprises an ELISA plate, PCPE purification column and/or other reagents. Further optionally, the kit may comprise one or more further reagents, such as, for example, buffer, colorimetric reagent and standard sample.

The biological sample for analysis by the method or kit of the present invention may comprise, for example, plasma, serum, urine, cerebrospinal fluid, cell extract, seminal plasma, blood, prostatic fluid, seminal fluid, semen, the external secretions of the skin, respiratory, intestinal, and genitourinary tracts, tears, sputum, saliva, milk, peritoneal fluid, pleural fluid, cyst fluid, broncho alveolar lavage, lavage of the reproductive system and/or lavage of any other part of the body or system in the body. Preferably, the sample is serum.

Optionally and preferably, proteins in the biological sample are separated by one or more techniques selected from the group consisting of electrophoresis (SDS-PAGE, IEF, 2DE), and chromatography (LC-LC, affinity column).

The PCPE pattern is preferably detected by contacting the separated biological sample with anti-PCPE antibody to form a complex of PCPE with the antibody, followed by detection of the complex or direct detection of PCPE protein by representative peptide pattern/profile. Detection may comprise, for example, visualization by colorimetric methods, such as first or secondary antibodies with fluorescence and/or alkaline phosphatase, ECL (by imaging or other methods), or mass spectroscopy (MS) and MS/MS analysis for direct mass detection.

In some embodiments, PCPE is useful as a quantitative biomarker. For quantitative analysis, a plurality of standards are preferably employed to determine a relative concentration curve. The tested concentration of PCPE from the serum of the subject is then compared to the standard concentration curve, in order to determine the relative concentration of PCPE in the serum of the subject. Greater accuracy may optionally and preferably be obtained through the provision of additional standard concentrations for the concentration curve. For example, such a concentration curve with standards may optionally be provided for an ELISA assay.

In some embodiments of the present invention, the type of sugars may optionally be determined, particularly since as described below, PCPE features a plurality of glycosylation sites which show differential sugars depending upon such factors as the age of the subject and so forth. Such differences between different sugars may optionally be obtained by treating PCPE from the serum of a subject with an enzyme or other treatment to alter the sugar content in a specific manner, for example by cleavage of a polysaccharide or portion thereof. The effect of such a treatment on the PCPE may optionally be determined through antibody binding, gel electrophoresis (as removing part or all of the sugars will typically affect the behavior of the protein during electrophoresis, particularly for IEF analysis but also optionally for 1D gels), column chromatography and so forth as is known in the art.

The method or kit of the present invention may be used for detection of disorders that relate to PCPE (i.e. regulation of fibrillar collagen synthesis), particularly bone diseases such as growth disorders (whether genetic or due to malnutrition etc), premature babies, aging, osteoporosis, bone cancer metastasis, and diagnosis of one or more of the following diseases: Paget's disease (excessive resorption of bone by osteoclasts, followed by the replacement of normal marrow by vascular, fibrous connective tissue), Osteomalacia, Rickets, bone tumors, osteoporosis, bone changes occurring due to parathyroid disorders, lymphoma and leukemia typing and in particular the identification of granular lymphocytic leukemia in the bone marrow and Sezary syndrome (an erythrodermic cutaneous T-cell lymphoma with a leukemic component), optionally as well as one or more erosive arthropathy, spondyloarthropathy, lytic bone lesions, and pathologic fractures, whether presenting as the primary disease or sequelae of a different disease process, including but not limited to hemodialysis-related amyloidosis, various diseases featuring renal dysfunction and amyloidosis without hemodialysis. Optionally and preferably, PCPE may be used to diagnose metastasis of cancer cells to bone or out of bone (ie metastasis of a bone related cancer from a primary site in bone tissue to one or more other locations in the body). Normal bone growth may optionally be measured and tracked. The method and kit of the present invention are also useful for detection of organ fibrosis (such as fibrosis of the liver, lung, heart etc), or any other type of fibrosis, whether genetic, cirrhotic (as for alcohol induced hepatic cirrhosis), idiopathic fibrosis, cardiac fibrosis, arterial blockages and/or fibrosis, and so forth.

PCPE may also, in at least some embodiments, be suitable as a clinical biomarker for a drug or other therapeutic treatment. For example, the effect of various treatments on the PCPE pattern in serum from experimental animals is described below. Furthermore, it was shown that the PCPE pattern changes in serum from children having growth problems before and after treatment with growth hormone. The PCPE pattern also changes in cell culture media before and after various treatments, such that PCPE would also be a useful research tool for in vitro experiments.

In other embodiments, PCPE is combined with one or more additional bone markers, such as BMP, alkaline phosphatase and so forth, to provide a more effective diagnostic profile and/or for determining the effect of one or more therapeutic treatments on a subject.

In still other embodiments, PCPE, alone or in combination with one or more other markers, is useful as a marker for determining cell state with regard to differentiation, particularly for osteoblasts and/or fibroblasts. Such a determination may optionally be performed ex vivo, for example for selecting and/or treating cells outside the subject's body, after which optionally the selected and/or treated cells are returned to the subject's body.

The methods and kits of the present invention are further useful in understanding changes in bone physiology that occur during growth, lactation, and menopause, which may optionally be useful for such applications as personalized medicine, tailoring drug regimens, early detection and treatment follow-up, and so forth, early diagnosis and follow-up of fibrillar disorder and diseases.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As used herein the term "about" refers to ±10%.

As discussed in greater detail in the Examples section below, PCPE in serum samples was studied following separation of serum by isoelectric focusing (IEF), SDS-polyacrylamide gel electrophoresis (SDS-PAGE) or two-dimensional electrophoresis (2DE), using IEF and SDS-PAGE combined. Preliminary results suggested that the IEF pattern of human serum PCPE (hsPCPE) may be a bone formation biomarker, however no information exists on the nature of the serum protein. Previous experiments with cell lines show that PCPE is processed into smaller active fragments following its secretion from the cell and undergoes multiple post-translation modifications[22].

Specific detection of PCPE was performed using immunoblotting or immunofixation with commercial PCPE antibodies, followed by silver staining for immunofixation or detection of immunoblot through secondary detection with horseradish peroxidase (HRP)-conjugated antibody and Enhanced ChemiLuminescence (ECL) detection. PCPE in adults, immature and mature babies was studied. A significant difference in the pattern of serum PCPE was detected between immature and mature babies. In adults, another pattern was observed.

As further shown in the Examples section below, changes were seen in the pattern and intensity of serum PCPE in breast cancer patients with bone metastasis.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods
Serum collection:

Human blood samples with no additives were collected from 35 adult breast cancer patients (25-80 years of age), with or without bone metastasis, in the oncology unit, or from prostate cancer patients or multiple myeloma cancer patients, all from Chaim Sheba Medical Center, Israel in a tube for blood collection (#367957) BD Vacutainer. Approval for the collection of samples was obtained from the institutional Ethics Committee. Informed consent was obtained from patients before collection. Serum was obtained by centrifugation, 10 min at 1200 g at room temperature (RT). Aliquot samples were stored at −80° C. until analysis. Blood was collected and stored in a similar manner from 12 children: four preterm babies, four term babies and four older children (age 6-9 years); or from children having growth problems; all at Schneider Children's Medical Center of Israel. Again, approval for the collection of samples was obtained from the institutional Ethics Committee; consent was obtained from parents or guardians as required for under-age minors.

Materials:

Molecular marker—ProSieve colored protein marker was purchased from Cambrex Bioscience.

Non fat dry milk (#170-6404), Tris buffer saline TBS×10, Premixed tris/glycine buffer×10, SDS solution 10% (#161-0416) and Polysorbate 20 (TWEEN 20; #170-6531) were purchased from BioRad.

Rat Anti human PCPE antibody (# MAB2627 and AF2627 were purchased from R&D Systems, Minneapolis, Minn., USA.

HRP-conjugated Goat anti rat IgG (#3140) and a chemiluminescent subtrstrate, SUPERSINGEL West Pico Chemiluminescent substrate (#34077), were purchased from Pierce.

Nitrocellulose (#401381) was purchased from Schleicher & Schuell (S&S). Methanol #1.06009.2500 was purchased from Merck.

Ready made isoelectric focusing polyacrylamide gels, PHASTGEL SDS-PAGE, IEF 3-9, IEF 5-8 (#17-0545-01, 17-0543-01 and 17-0623-01 respectively), Ready made SDS polyacrylamide gels. PHASTGEL™ Buffer strips-SDS (17-

0516 -01), and PlusOne silver stain kit (#17-1150-01) were purchased from Amersham Biosciences.

Tube for blood collection (#367957) BD VACUTAINER.

Peptide:N-Glycosidase F (PNGase F) (#P0705S) and Neuraminidase (#0720S) were purchased from New England BioLab.

Lectin binding arrays of Procognia (Israel) Ltd. were used as directed by the manufacturer. More details of these arrays and of their method use are provided in "A lectin array-based methodology for the analysis of protein glycosylation", by Rosenfeld et al, J. Biochem. Biophys. Methods 70 (2007) 415-426, which is hereby incorporated by reference as if fully set forth herein.

Immunoblotting was performed using western blotting as follows. Following gel electrophoresis, the proteins were transferred to nitrocellulose paper with a transfer buffer consisting of 25mMTris, 129mMglycine, 20% methanol, and 0.1%SDS. PCPE1 was identified using a specific anti-human PCPE1 antibody (MAB2627; R&D Systems, Minneapolis, MN, USA). The secondary horseradish peroxidase (HRP)-conjugated antibody (31470; Pierce Biotechnology) was diluted 1:10,000 in Tris-buffered saline containing 0.05% (v/v) Tween-20. Antigenic expression was visualized by the chemiluminescent substrate SUPERSIGNAL West Pico chemiluminescence substrate (34077; Pierce Biotechnology) followed by exposure to X-ray film (Kodak. Rochester, NY. USA) according to the instructions of the manufacturer.

Rat and Mouse Experiments—Calorie Restriction

Both rats and mice were subject to an initial phase of calorie restriction of up to 40% reduction in permitted calories. Next, the animals were permitted to eat ad libitum, such that their caloric intake increased above normal to allow the animals to overcome the previous restriction. Serum samples were drawn in a similar manner to that described for human patients above, and PCPE patterns were determined as described herein.

Digestion of Serum Samples with PNGase F and Neuraminidase

A serum sample of 1.5 µl was incubated with 75 U PNGase F or 50 U neuraminidase (P0705S and P0720S respectively; New England Biolabs, Ipswich, MA, USA) overnight at room temperature, according to the instructions of the manufacturer.

SDS-Polyacrylamide Gel Electrophoresis (PAGE)

Serum samples (2 µl at 1:30 dilution) were separated in PHASTGEL homogeneous 12.5% commercial precast gel using PHASTGEL SDS Buffer strips in the electrophoresis workstation PHASTSYSTEM (Amersham Biosciences, Piscataway, NJ, USA). The method was performed according to the instructions of the manufacturer.

Two-dimensional Gel Electrophoresis (2DE)

Serum samples were depleted of albumin and immunoglobulin (depletion kit #89876; Pierce Biotechnology, Rockford, IL, USA) and loaded onto an IMMOBILIN Dry Strip (pH-3-10) (Amersham Biosciences, Piscataway, NJ, USA), on a PROTEAN-IEF Cell for the first dimension and a PROTEAN IIXI 2-D Cell (both from Bio-Rad Laboratories, Hercules, Calif.) for the second dimension.

Isoelectric Focusing (IEF)

Serum samples (2µl at 1:3 dilution) were separated using ready made isoelectric focusing polyacrylamide gels PHASTGEL IEF pH 3-9, pH 4.25-6.5 or pH 5-8 commercial precast gels in the electrophoresis workstation PHASTSYSTEM (Amersham Biosciences). The method was performed according to the instructions of the manufacturer.

Mass Spectroscopy (MS)

MS studies were generally performed as described in "Sample preparation for serum/plasma profiling and biomarker identification by mass spectrometry"; Jose L. Luque-Garcia, Thomas A. Neubert; Journal of Chromatography A, 1153 (2007) 259-276; hereby incorporated by reference as if fully set forth herein.

SaoS-2 and 293 T

Cells were maintained in Dulbecco's modified Eagle's medium (DMEM) with 10% fetal bovine serum. Air, 95%; carbon dioxide (CO2), 5% and temperature, 37.0° C.

Recombinant human PCPE produced by NSO cells was bought from R&D Systems Europe (United Kingdom). In all Examples below, reference to "rhPCPE1" or recombinant human PCPE/PCPE1 is to this protein, with the exception of PCPE produced by 293 T cells (as described below).

Example 1

Human PCPE Analysis

Purified, isolated recombinant human PCPE1, as well as human serum PCPE1, was analyzed by various methods. The results are shown in FIGS. 1A-E. As shown, FIG. 1A shows LC-MS/MS analysis of recombinant human PCPE 1. The analysis covered nearly 60% of PCPE1 amino acid (aa) sequence. Only three regions were not detected by MS analysis. Two of them contain the potential site for N-glycosylation of hPCPE1 (amino acid residues 29 and 431). Glycosylated peptides cannot be identified after MS analysis because the glycan changes the peptide mass and charge. FIG. 1B shows a list of peptides obtained from LC-MS/MS from serum human PCPE1 (shPCPE1) after partial purification on a heparin column; total coverage was 41%. These results are similar to those obtained for fully purified recombinant human PCPE1.

FIG. 1C relates to the presence or absence of various saccharides, which were detected by using the lectin binding arrays of Procognia (Israel) Ltd. as described above, indicating that recombinant human PCPE1 has complex bi-antennary sialylated N-glycans. As described in greater detail below, for diagnostic purposes there may be changes in structure of saccharides and/or in presence or absence thereof. Such changes have been described for other diagnostic proteins (biomarkers), for example in "Altered glycosylation pattern allows the distinction between prostate-specific antigen (PSA) from normal and tumor origins" by Peracaula et al, Glycobiology vol. 13 no. 6 pp. 457±470, 2003, which is hereby incorporated by reference as if fully set forth herein. In this article, PSA was shown to have a different glycopattern (ie different glycans or saccharides) from prostate tumor cell lines as opposed to PSA obtained in normal seminal fluid. Such differences in the glycopattern of PCPE, including human serum PCPE1, are also encompassed by at least some embodiments of the present invention. Putative or potential glycopattern differences in PCPE1 taken from the sera of patients with a bone or bone related disease, as opposed to normal serum, are described in greater detail below.

Figure 1E:
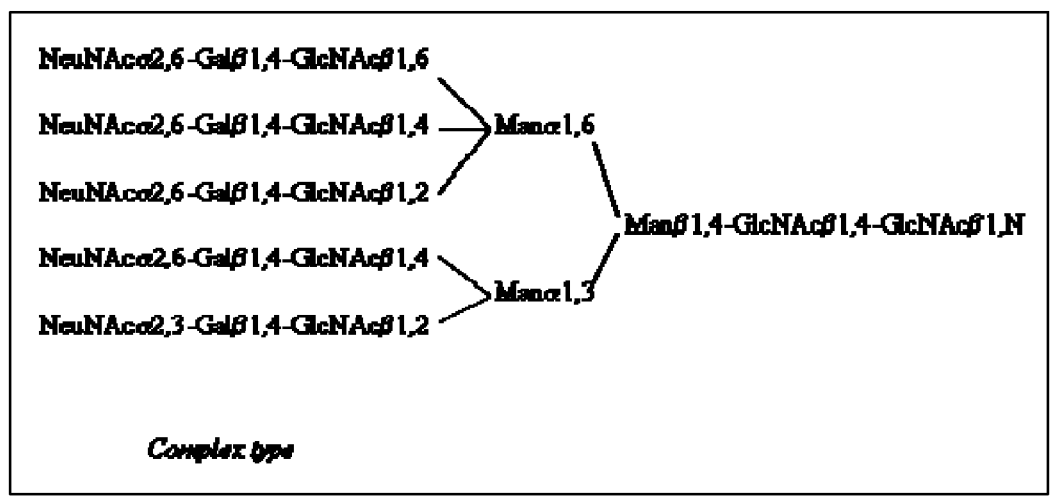

FIG. 1D shows the HPLC elution profiles of glycans derived from recombinant human PCPE1 expressed by NSO cells. N-glycans were prepared from purified hPCPE1, derivatized and separated on the positively charged column. The elution retention time of the glycans show that they have extensive amounts of sialic acid. FIG. 1E shows complex-type biantennary N-glycans, of the type which are found on rhPCPE1 as supported by the above results.

Example 2

Human Serum SDS-PAGE Pattern

Serum samples (2µl at 1:3 dilution) were separated in homogeneous 12.5% commercial precast gel using PHAST-GEL SDS Buffer strips in the electrophoresis workstation PHASTSYSTEM, Amersham Biosciences, and PCPE was detected by immunoblotting with specific anti-PCPE antibody. The method was performed as per the instructions of the manufacturer.

Figure 2:
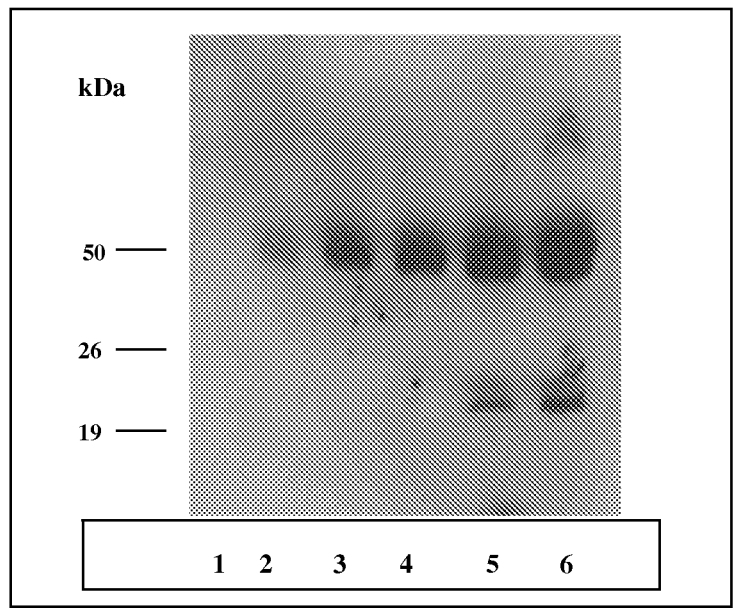
FIG. 2 shows an SDS-PAGE pattern for Human Serum PCPE.

The SDS-PAGE pattern obtained is shown in FIG. 2

Example 3

Human Serum IEF Pattern

Figure 3:
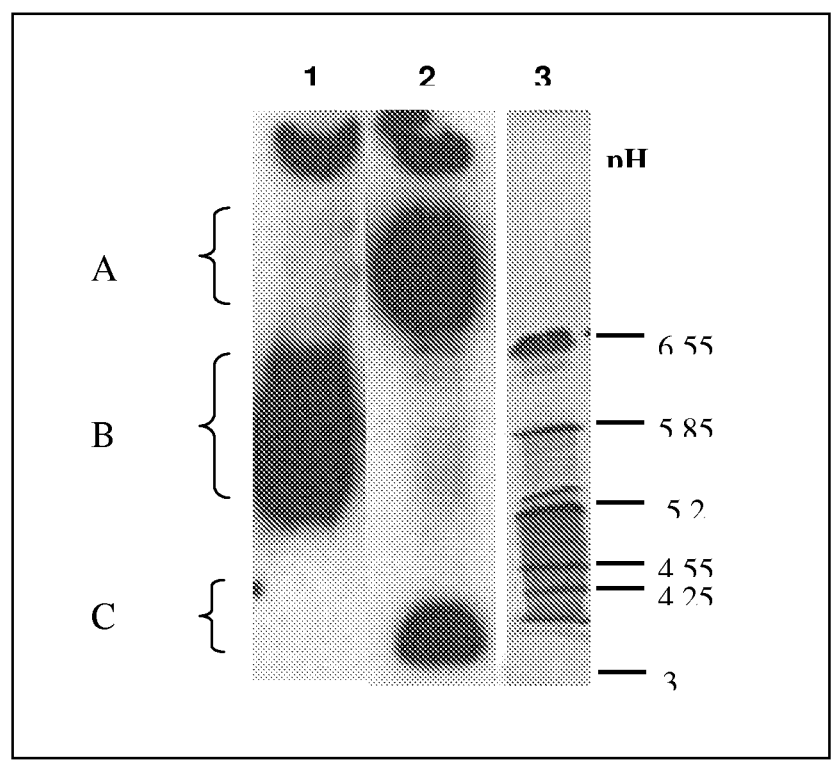
FIG. 3 shows an IEF 3-9 pattern for Human Serum PCPE.

Serum samples (20µl at 1:3 dilution) were separated in PHASTGEL IEF 3-9, commercial precast gels in the electrophoresis workstation PHASTSYSTEM, Amersham Biosciences. PCPE was detected by immunoblotting with specific anti-PCPE antibody. The method was performed as described above for Example 2. Results are shown in FIG. 3.

Example 4

Sensitivity of Human Serum PCPE, IEF Pattern, to Peptide:N-Glycosidase F (PNGase F)

A serum sample 1.5 µl was incubated with 75 U of the enzyme PNGase F (lane 2 FIG. 4) or without the enzyme (lane 1 FIG. 4) over night at room temperature according to the enzyme manual. Samples were than separated on IEF gel (pH range 5-8). PCPE was detected by immunofixation with specific antibody. Immunofixation was performed by applying anti-PCPE to the gel after IEF. The interaction of PCPE with its specific antibody results in precipitation of PCPE-antibody complex, which thereby fixes the PCPE to the gel. All other proteins were subsequently washed out of the gel with water, overnight with agitation, and the complexes were detected by protein silver staining (PlusOne silver stain kit Amersham Biosciences)[24].

Figure 4:
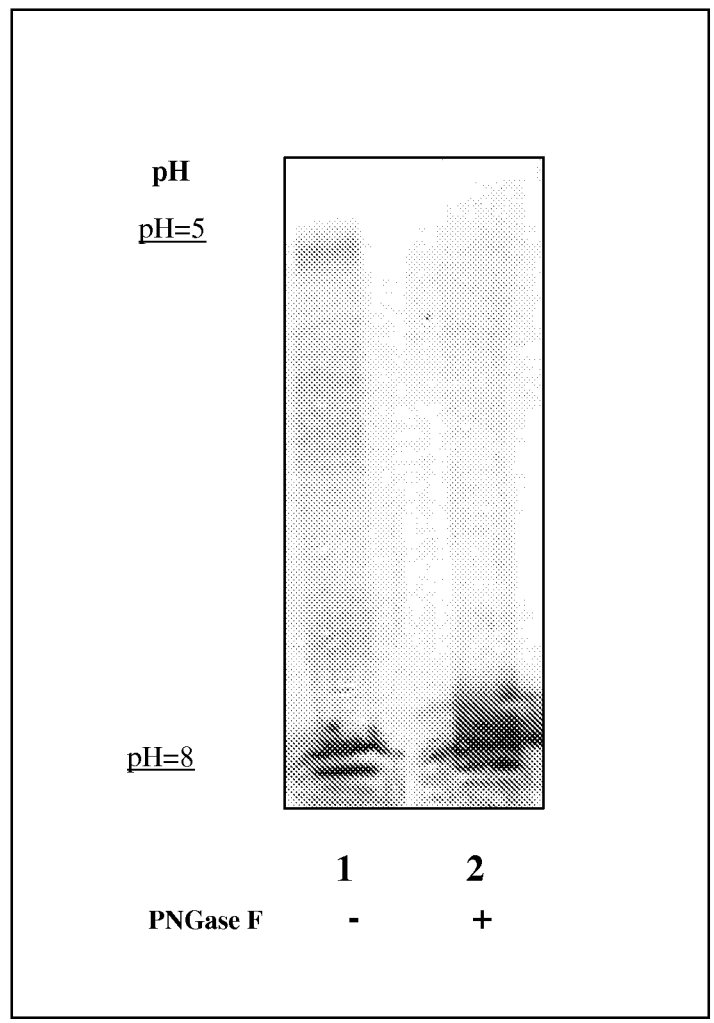
FIG. 4 shows the effect of PNGase F on the IEF pattern of Human Serum PCPE.

The IEF pattern obtained is shown in FIG. 4.

Example 5

Sensitivity of Human Serum PCPE, IEF Pattern, to Neuraminidase

A serum sample 1 µl was incubated with 50 U of neuraminidase (lane 1 FIG. 4) or without the enzyme (lane 2 FIG. 5) over night at room temperature according to the enzyme manual. Samples were then separated on IEF gel (pH range 4-6.5). PCPE was detected by immunofixation with specific antibody as described before.

Figure 5:
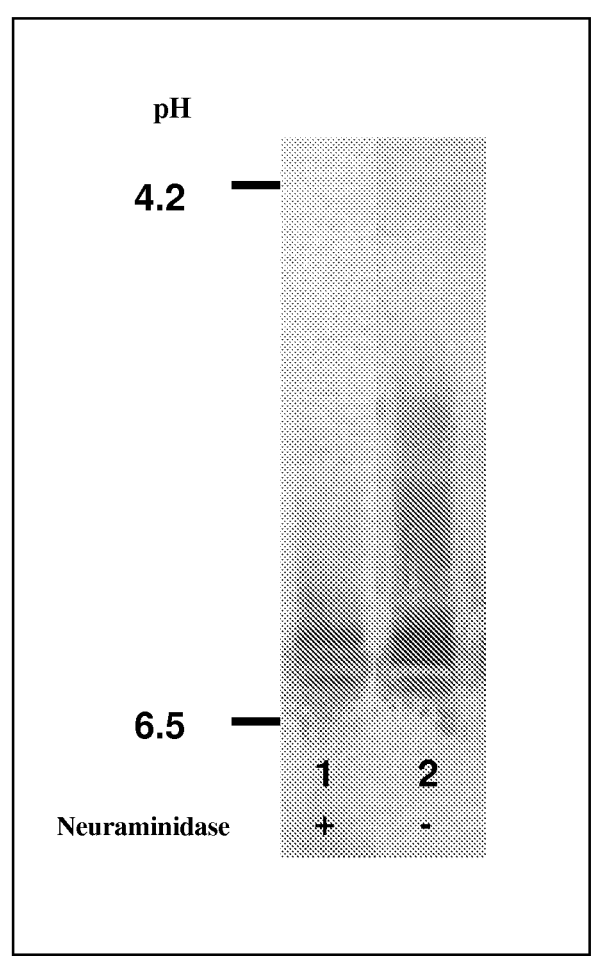
FIG. 5 shows the effect of Neuraminidase on the IEF pattern of Human Serum PCPE.

The IEF pattern obtained is shown in FIG. 5.

Example 6

Human Serum 2 Dimensional Electrophoresis Pattern

Serum sample was depleted from Albumin and Immunoglobulin. The sample was than subjected to 2-dimensional electrophoresis (2DE) using the IMMOBILINE Dry Strip (pH-3-10) (Amersham) on a PROTEAN IEF Cell (Bio-Rad) for the first dimension and the PROTEAN IIXI 2-D Cell (Bio-Rad) for the second. Sample was separated on two gels in parallel. Following to the electrophoresis, one gel was subjected to western blot analysis with anti PCPE in order to detect PCPE positive spots (FIG.6B). The other gel was stained for protein detection with silver stain (FIG.6A). The spots marked with white circles were analyzed by MALDI Tof.

Figure 6:
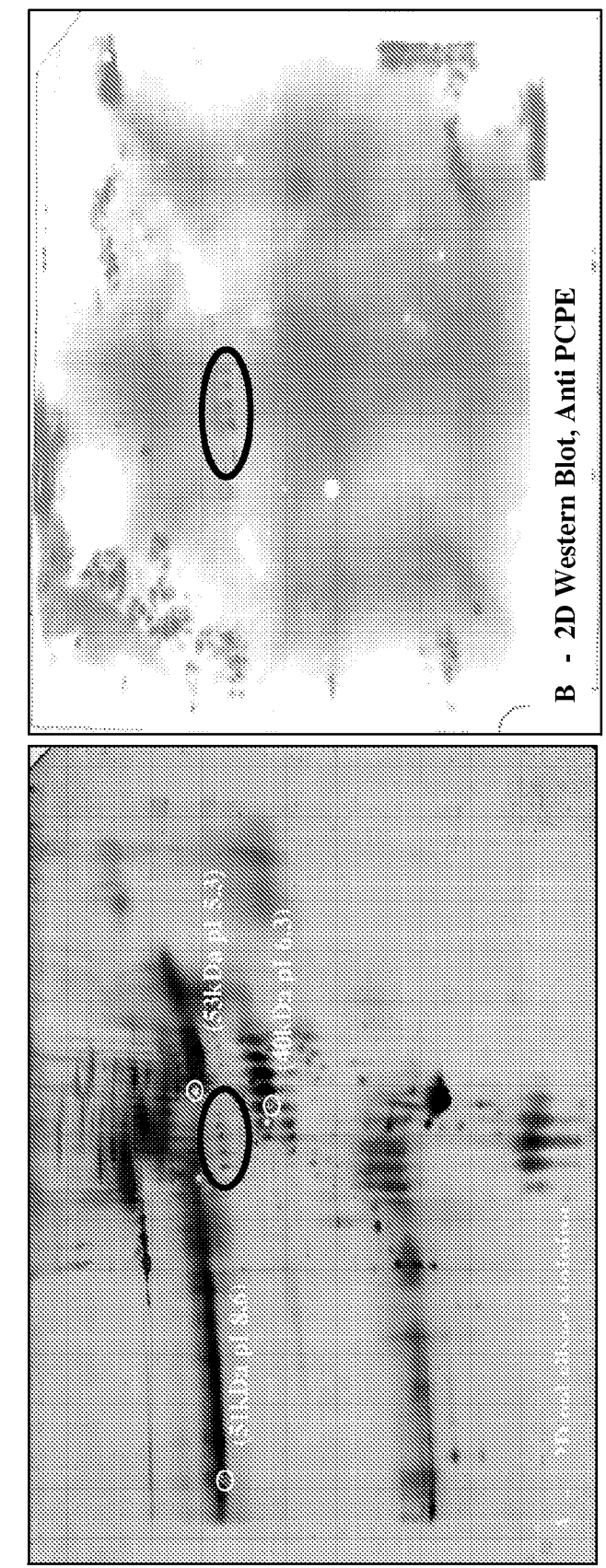
FIG. 6 shows a 2DE pattern for Human Serum PCPE.

The 2DE pattern obtained is shown in FIG. 6.

This technique separates the proteins in two steps according to two independent properties: the first-dimension is isoelectric focusing (IEF) which separates proteins according to their isoelectric points (pI); the second-dimension is SDS-polyacrylamide gel electrophoresis (SDS-PAGE) which separates proteins according to their molecular weights (Mw). Following reduction, alkylation and trypsin digestion, PCPE positive spots from the gel were analyzed by MS/MS in order to get preliminary information about the protein sequences. Part of this work was performed in the protein analyzing department in Tel Aviv University.

Example 7

Growth Dependency of Human Serum PCPE IEF Pattern

Figure 7A:
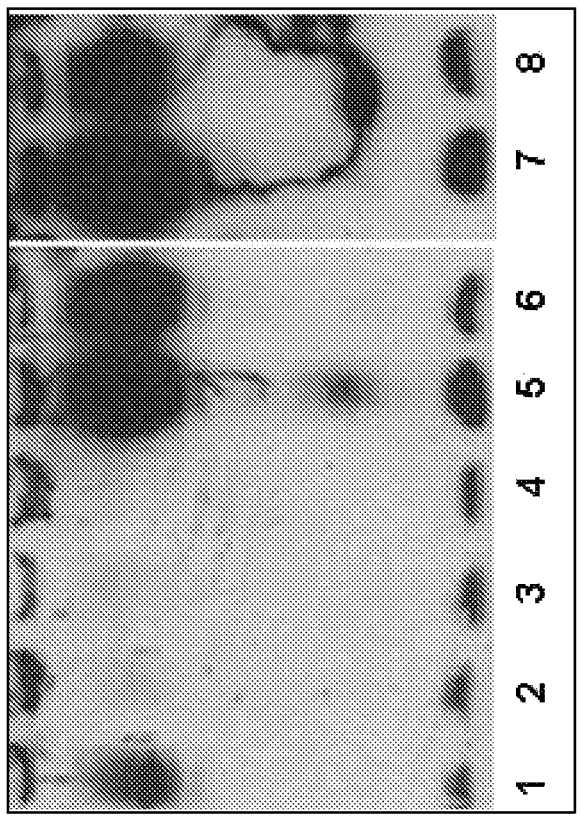
FIGS. 7-C show IEF patterns for Human Serum PCPE obtained from immature babies and children with growth complication.
Figure 7B:
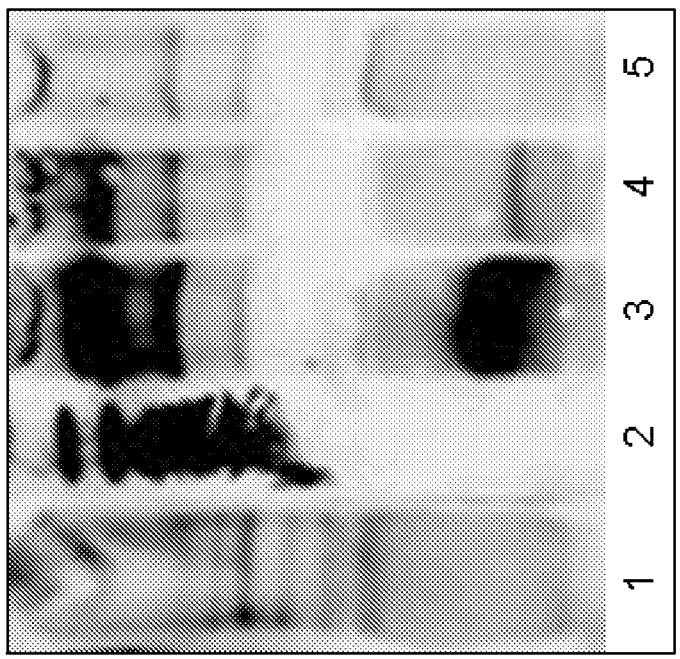

Human serum samples from 4 preterm babies and 4 term babies were separated on IEF gel (pH range 3-9). PCPE was detected by immunoblot with specific antibody for FIG. 7A. The IEF pattern obtained is shown in FIG. 7A. Lanes 1-4 feature serum from preterm infants, while lanes 5-8 feature serum from term infants; PCPE was detected by immunoblot with the previously described specific antibody. FIG. 7B shows the IEF gel with immunoblotting, in which lane 1 shows adult normal serum; lane 2 shows rhPCPE1 and lanes 3-5 show serum from a single significantly premature infant at days 3, 40 and 82 respectively.

Figure 7C:
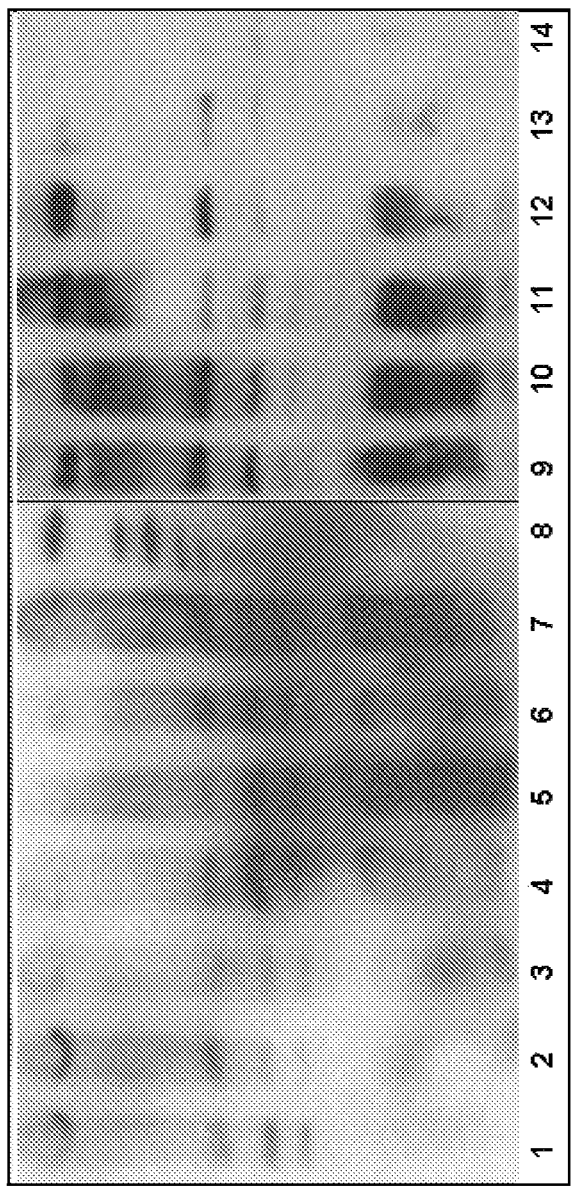

In addition, human serum PCPE patterns were obtained from children treated with GH (growth hormone). Children treated with growth hormone experience additional and/or accelerated growth of body tissues, including of bone tissue. To determine the pattern of PCPE found in human sera taken from such children, human sera samples from such children were subjected to IEF as previously described. Samples were separated on IEF gel (pH range 3-9) as described in Example 3 above. PCPE was detected by immunoblot with specific antibody as previously described. As shown in FIG. 7C, lane 1 shows adult normal serum. Lane 8 shows rhPCPE1. Lanes 2-3; 4-5; 6-7; 9-10; 11-12; 13-14 show the results of serum samples from children diagnosed as suffering from growth problems. Lanes 3, 5, 7, 10, 12, 14 shows serum samples that were taken before GH treatment and 2, 4, 6, 9, 11, 13 show serum samples that were taken three months after GH treatment. Clearly GH treatment causes a change in the PCPE pattern, which may be due to changes glycosylation although it is possible that different changes may be occurring, additionally or alternatively.

Example 8

Correlation of Human Serum PCPE IEF Pattern with Bone Metastasis

Serum samples from breast cancer or prostate cancer patients were separated on IEF gel (pH range 3-9). PCPE was detected by immunoblot with specific antibody.

Figure 8:
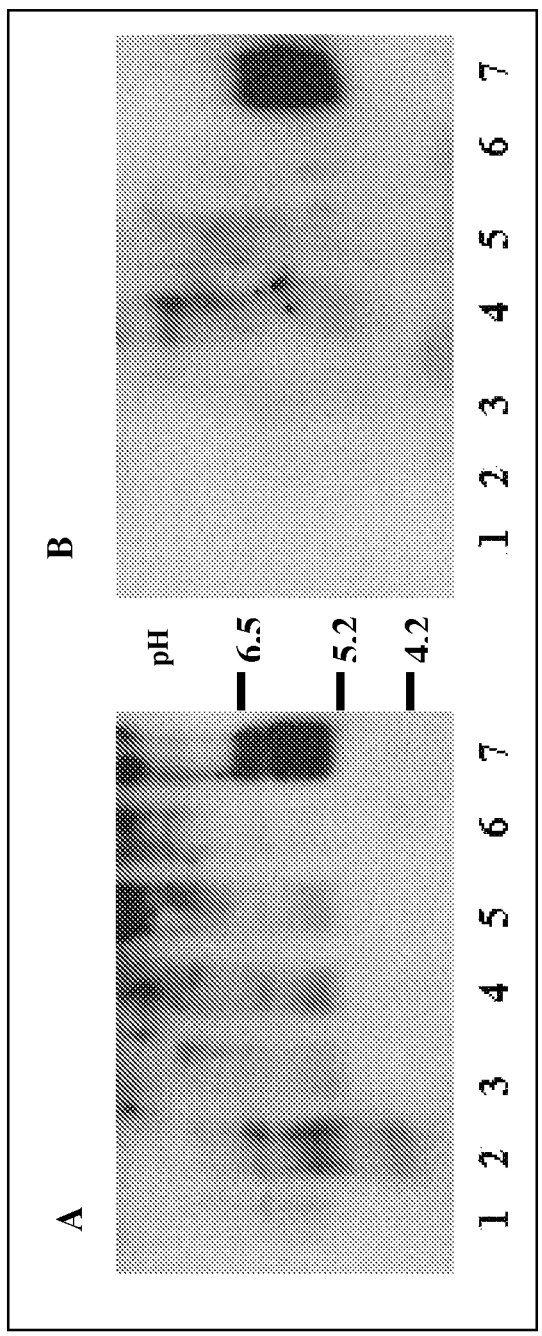
FIGS. 8 and 9 shows IEF patterns for Human Serum PCPE obtained from subjects with and without bone metastasis.
Figure 9:
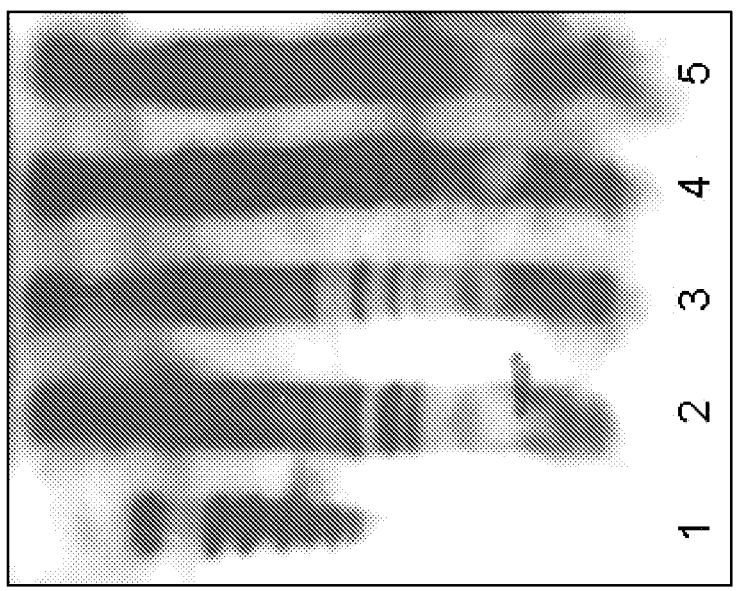

The IEF pattern obtained is shown in FIG. 8 for breast cancer patients and FIG. 9 for prostate cancer patients.

FIG. 8A: Lanes 1-6 show patterns from serum from breast cancer patients with bone metastasis. FIG. 8B: Lanes 1-6 show patterns from serum from breast cancer patients with no metastasis in the bone. FIGS. 8A and 8B: Lane 7 is a positive control for A and B.

FIG. 9: Lane 1 shows recombinant human PCPE1 as a positive control. Lane 2 shows normal serum as a negative control. Lanes 3-5 show serum from patients with prostate cancer, in which serum in lanes 3 and 5 is from patients with bone metastasis and serum in lane 4 is from patients without bone metastasis.

Example 9

Structural Analysis of PCPE

Carbohydrate side chains of glycoprotein play critical roles in numerous biological systems[25]. Therefore information concerning the carbohydrate side chains is of great importance. Towards this purpose, PCPE is purified from serum by immunoaffinity chromatography. The purified protein is analyzed using Tandem Mass Spectrometry (MS/MS) in order to define exact amino acid sequence and to detect glycosylation sites. To elucidate the nature of oligosaccharide chain, the purified protein is digested using endoglycosidases [Endo H, Peptide:N-Glycosidase F (PNGase-F)] and exoglycosidases (Mannosidase, Neuraminidase) and O-glcosydase followed by analysis using the same methods.

Example 10

Osteoblast-specific Pattern of PCPE

Figure 10:
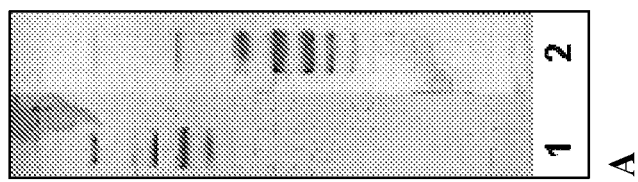
FIGS. 10A-10B show PCPE patterns from different cell lines.
Figure 10:

To define an osteoblast specific pattern of PCPE, cell lines were grown, and media was collected from the different cell lines and concentrated with a centricon device. Samples were separated on IEF gel (pH range 3-9) as described in Example 3 above, and the specific cell pattern was analyzed. PCPE was detected by immunoblot with specific antibody as previously described. The results are shown in FIGS. 10A-B. For FIG. 10A, proteins were separated on IEF (pH range 3-9) and detected by silver stain. Lanes 1 and 2 show rhPCPE1 expressed in NSO and 293 T cell lines respectively. For FIG. 10B, media was collected from the SaoS-2 cell line. The media was concentrated with a centricon device and separated on IEF gel (pH range 3-9). PCPE was detected by immunoblot with specific antibody as described above. Lane 1 shows rhPCPE from the NSO cell lines. Lane 2 shows hsPCPE 1. Lane 3 shows SaoS-2 cell line medium.

The results demonstrate that the serum PCPE is mainly from bone. Furthermore, PCPE from bone cancer samples also has a similar appearance to that of normal bone and hence also serum. However, other cell lines show different results which are presumably due to different glycosylation patterns. Although the concentration may not change, the glycosylation pattern may change between different tissues as shown by these results. Without wishing to be limited by a single hypothesis, it is also possible that the different isoforms (with different glycosylation patterns) show different levels of activity.

Example 11

Human Serum PCPE Patterns Obtained from Multiple Myeloma Patients

Figure 11:
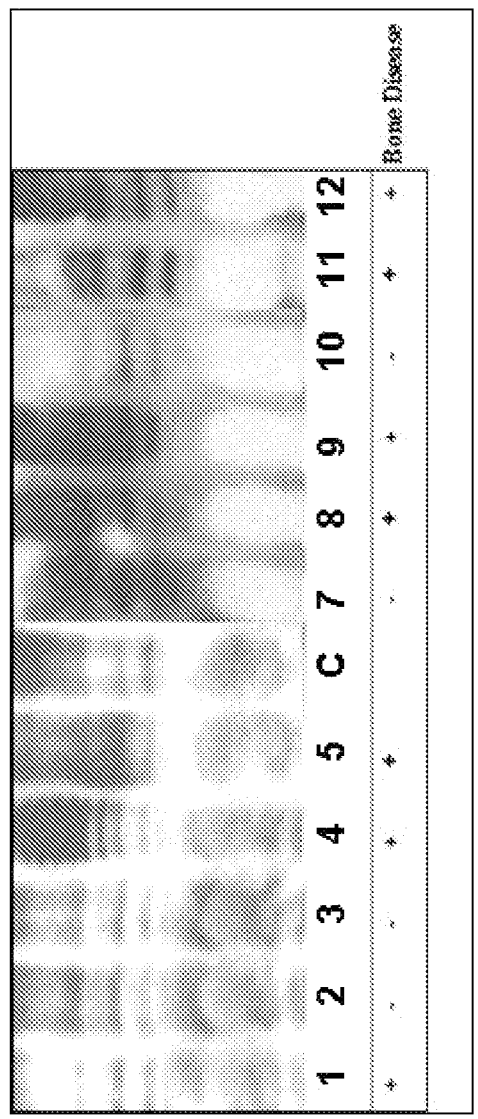
FIG. 11 shows sera from multiple myeloma cancer patients, as compared to sera from patients with other types of bone disease.

Multiple myeloma is a cancer of the bone, and more specifically of the bone marrow. To determine the pattern of PCPE found in human sera taken from such patients (as opposed to patients in which metastasis to bone occurs, in which the primary cancer site is not located in the bone), human sera samples were subjected to IEF as previously described. Samples were separated on IEF gel (pH range 3-9) as described in Example 3 above. PCPE was detected by immunoblot with specific antibody as previously described. As shown in FIG. 11, lanes 1-12 show the PCPE pattern in sera from multiple myeloma cancer patients. Lanes 1, 4, 5, 8, 9, 11 and 12 show sera taken from patients with bone disease, while lanes 2, 3, 7 and 10 show sera taken from patients without bone disease. Lane C shows adult normal serum. As shown by these results, PCPE from multiple myeloma patients shows significant differences in the isoforms for patients suffering from active bone disease as opposed to patients in which bone disease is not active.

Example 12

Human Serum PCPE Patterns Obtained from Adults with Bone Disease

There are various bone diseases which may affect adults, apart from cancer, such as osteoporosis and so forth. To determine the ability of PCPE to act as a biomarker for such diseases, human sera samples from adults with bone disease were subjected to IEF as previously described. Samples were separated on IEF gel (pH range 3-9) as described in Example 3 above. PCPE was detected by immunoblot with specific antibody as previously described. As shown in FIG. 13, lanes 1-6 show serum obtained from patients with a bone disease related to problems of bone metabolism. Lane C shows adult normal serum control, while R relates to recombinant PCPE. The pattern clearly differs between patients suffering from the bone disease and serum from a normal adult.

Example 13

PCPE Patterns Detected in Non-Human Animals after Various Interventions

It is possible to perform many direct interventions with non-human animals as part of experimental testing which naturally would not be possible with human subjects. Therefore, the effect of various interventions on PCPE patterns in such animals, all from mammalian subjects, was determined. Sera samples from such non-human animals were subjected to IEF as previously described. Samples were separated on IEF gel (pH range 3-9) as described in Example 3 above. PCPE was detected by immunoblot with specific antibody as previously described.

IEF patterns for rat serum PCPE were obtained from animals after treatment, which featured initial calorie restriction, followed by adding back such calories to provide increased food intake. IEF patterns for mouse serum PCPE were also obtained from animals after such treatment, again featuring initial calorie restriction, followed by adding back such calories to provide increased food intake. Briefly, PCPE patterns changed in animals before and after calorie restriction, indicating that specific interventions or treatments cause specific changes in PCPE patterns (data not shown). All experiments involved duplicate animals which displayed similar results. IEF patterns for rat and mouse PCPE were determined in media obtained from mesenchymal stem cells, as well as in osteoblasts, demonstrating that PCPE is secreted by both types of cells (data not shown).

Results and Discussion

The results of FIGS. 1A-1E support the determination that recombinant human PCPE1 has complex bi-antennary sialylated N-glycans. Such glycosylation may optionally form an important biomarker, as changes in glycosylation pattern have been shown to be disease related and/or diagnostically specific for other diseases, such as for example PSA glycosylation patterns for prostate cancer and transfferin in congenital disorder of glycosylation (CDG).

As shown in FIG. 2, serum separation on SDS-PAGE gel yielded two bands of hsPCPE, at ~50 kDa and ~22 kDa molecular weight.

PCPE is naturally processed into N-terminal fragments 34 kDa and 36 kDa, both of which also enhance procollagen C-proteinase activity of BMP-1. A 16.5 kDa protein corresponding to a C-terminal fragment of PCPE (known as the netrin (NTR) like fragment) has been described and shown to inhibit matrix metalloproteinase[21]. The band at 50 kDa is probably the holoprotein, and the band at 22 kDa has a molecular weight similar to that of the NTR fragment. No further bands were identified in the serum, which may have occurred because the antibody did not recognize the 30 kDa fragment or that the fragment is missing in the blood.

As shown in FIG. 3, separation of serum samples on IEF gel shows the appearance of multiple bands at three pI zones (zone A at above pH 6.5, zone B at pH 5.2-6.5, and C at pH 3-4.25). The molecular weight, as calculated from the 424 amino acid hPCPE protein deduced from the cDNA sequence is 45.5 kDa (pI 7.55), as seen in Table 1. The actual molecular weight of hsPCPE that is separated on SDS-PAGE is ~50 kDa (FIG. 1), and pI 6.5[26]. It has previously been shown for recombinant human (rhPCPE) that the difference between molecular weight (Mw) calculated by amino acid sequences and the Mw in SDS-PAGE, is due to post translational modifications, N-linked oligosaccharides decorated with sialic acid[22]. As mentioned above, PCPE is naturally processed into fragments 34 kDa-36 kDa, and 16.5 kDa. Theoretically, calculation of the pI's of these fragments, yields pI points 5.5 and 9.44 respectively, as seen in Table 1. The IEF pattern of hsPCPE only partially matches to theoretical pI points, and is more complex.

Complex IEF patterns/profiles are observed for many proteins. Some of the factors that influence the heterogeneity of IEF profiles in glycoproteins are differences in glycosylation, glycation, deamidation, and protein conformation. Among these factors, charge heterogeneity due to variation in glycosylation, in particular sialylation, sulfation, and phosphorylation, plays a major role in determining the IEF behavior of glycoprotein subpopulations.

PCPE contains two potential sites for N-linked glycosylation[20], the first is on amino acid 29 in the first CUB domain (included in the whole protein and 34-36 kDa fragments) and the second is at amino acid 431 in the NTR region (included in the whole protein and the 16.5 kDa fragment). Thus it was assumed that PCPE IEF pattern in the serum is a combination of different molecular weights and different oligosaccharide chains.

Two dimensional electrophoresis (2DE) and tandem mass spectroscopy (MS) were used to define the exact protein sequences of PCPE and its fragments in the serum. Protein sequences of PCPE and its fragments in the human serum were determined, in order to define their glycosylation site and analyze their carbohydrate chains.

Carbohydrate side chains of glycoprotein and posttranslational modification play critical roles in numerous biological systems[25]. Therefore information concerning the carbohydrate side chains is of great importance. To elucidate the nature of oligosaccharide chain the serum protein was digested using endoglycosidase Peptide:N-Glycosidase F (PNGase-F)] and exoglycosidase Neuraminidase (see Examples 4 and 5 digestion of the serum sample, with PNGase F and Neuraminidase, prior to gel separation, was used to show that the hsPCPE multiple band appearance is due to N-linked glycosylation decorated with sialic acid respectively. PNGase F cleaves between the innermost N-acetylglucosamine (GlcNAc) and asparagine residues of high mannose, hybrid, and complex oligosaccharides from N-linked glycoproteins. Neuraminidase catalyzes the hydrolysis of $\alpha$2-3, $\alpha$2-6, and $\alpha$2-8 linked N-acetyl-neuramic acid residues from glycoproteins and oligosaccharides.

Sensitivity of Human Serum PCPE, IEF pattern, to Peptide:N-Glycosidase F (PNGase F) is shown in FIG. 4. Treatment of serum with PNGase F resulted in disappearance in mobility shifts of PCPE on IEF 5-8 gel (lane 2 FIG. 4), suggesting that hsPCPE has N-linked oligosaccharides.

Sensitivity of Human Serum PCPE, IEF pattern, to Neuraminidase is shown in FIG. 5. Neuraminidase resulted in disappearance in mobility shifts of PCPE on IEF 4-6.5 gel (lane 1), suggesting that hsPCPE N-linked oligosaccharides are decorated with sialyl residues. These results also support the determination of the glycosylation pattern as featuring complex bi-antennary sialylated N-glycans, as determined through MS analysis, column chromatography and lectin array analysis.

Human serum 2 Dimensional Electrophoresis pattern is shown in FIG. 6. As discussed above and shown in FIG. 2, separation of serum sample on IEF gel shows the appearance of multiple bands at three pH zones (zone A—above pH 6.5; zone B—ph 5.2-6.5; and zone C— pH 3-4.25). Separation of adult serum by 2DE as determined by western blot analysis yielded a pattern of 5 positive spots at pH 5.3-6.8 (shown as black circles in FIG. 6B) with molecular weight of ~50 ~53 kDa (shown as circles in FIG. 6A). Mature babies (lanes 8-11) have strong bands in two pH range zone, A and zone C and faint bands in zone B. Immature babies (lanes 4-7) on the other hand have major bands at pH zone C with faint appearance of bands at zone A. Bone disease of prematurity is a complication of preterm birth[27], hence it seems that PCPE has a unique band appearance in premature infants.

FIGS. 7A and 7B show the different PCPE patterns in preterm babies vs term babies (FIG. 7A), while FIG. 7B relates to multiple samples taken from a premature baby from birth and during a three months' following period that the baby remained in the hospital. The premature baby was born significantly before term, while the preterm babies were only born a few weeks early. In both cases, the PCPE pattern changes in a correlated manner with bone development as the ossification process continues.

As another example of an effect of growth and/or treatments for inducing growth on the PCPE pattern, FIG. 7C shows that growth hormone treatment of children having growth problems causes a change in the PCPE pattern (when comparing sera taken before and after the administration of growth hormone), which may be due to changes glycosylation although it is possible that different changes may be occurring, additionally or alternatively.

As can be seen in FIG. 8A, in serum from breast cancer patients, PCPE bands were mainly identified at zone B (pH 5.2-6.5). IEF separation of serum samples from patient without bone metastasis shows faint or no appearance of PCPE bands (FIG. 8B, lanes 1-6). Similar results are shown in FIG. 9 for prostate cancer patients with or without metastatic bone disease.

It is important to note that all patients with bone metastases are treated with bisphosphonates. Bone metastases are classified as either osteolytic (excessive bone resorption), osteoblastic (excessive bone formation), or mixed, based on their radiographic appearance. However, most blastic metastases have resorptive component, and most lytic lesions are accompanied by some attempt, albeit incomplete, of repair of bone formation[28]. Bone metastases from prostate cancer are predominantly osteoblastic, whereas metastatic lesions in bone from breast cancer can be osteoblastic, osteolytic, or mixed. Thus, high intensity of PCPE band in patient with bone metastases may result from osteoblastic activity in bone.

FIG. 10A shows rhPCPE1 expressed in NSO (mouse myeloma) and 293T (kidney embryonic) cell lines respectively. FIG. 10B compares NSO (mouse myeloma) and SaoS-2 (human bone osteosarcoma) cell lines. These results show that mouse myeloma produces PCPE with different (and presumably defective) sialylation, as compared to recombinant human PCPE1. As noted above, PCPE has a significant amount of sialic acid glycosylation.

FIG. 11 shows that PCPE from multiple myeloma patients has significant differences in the isoforms for patients suffering from active bone disease as opposed to patients in which bone disease is not active.

Figure 12:
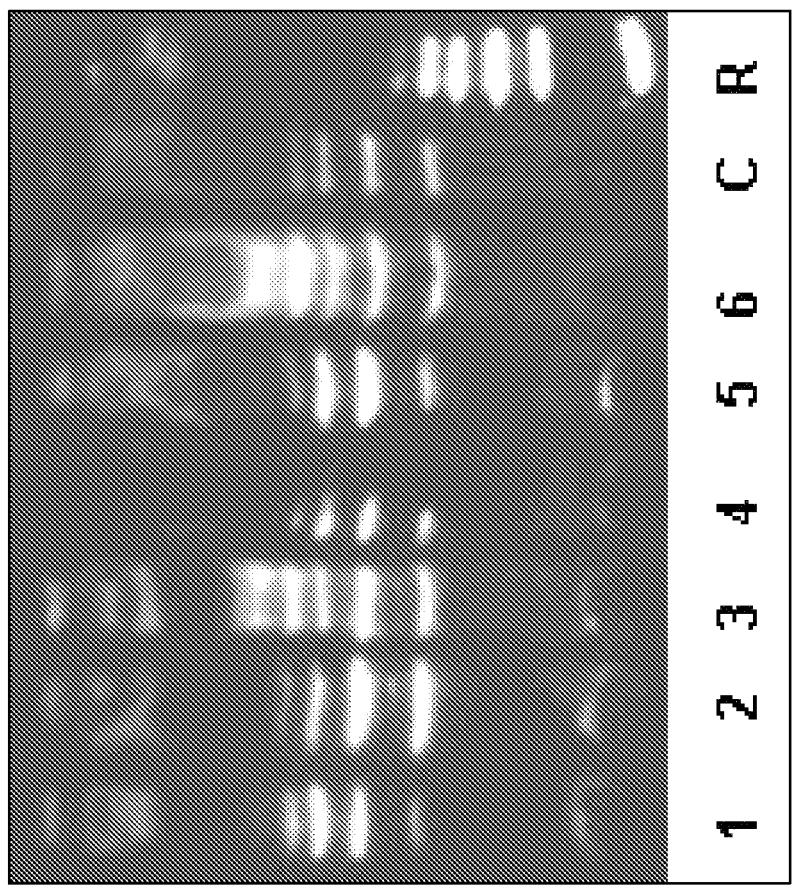
FIG. 12 shows sera from patients suffering from a disease of bone metabolism.

FIG. 12 shows that patients suffering from bone metabolism disease have a different PCPE isoform pattern than the pattern found in normal adult serum.

selection or as a clinical endpoint marker (for example for determining the efficacy of a drug in a clinical trial and/or for treating a patient).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

TABLE 1

Summary of human PCPE molecular weight (Mw) and isoelectric points (pI).

| | Protein | Amino Acid | Potential N-Glycosylation sites (aa) | Predicted from Sequence Mw (kDa) | Predicted from Sequence pI | From Gel Mw (kDa) | From Gel pI |
|---|---|---|---|---|---|---|---|
| Recombinant human PCPE | PCPE | 26-446 | 29, 431 | 45.5 | 7.55 | 55 (Ref 13) | 5.5-6.5 (Lab) |
| | N-terminal fragment (CUB 1 + 2) | 26-300 | 29 | 29.6 | 5.5 | 34, 36 (Ref 13) | ND |
| | C-terminal fragment (NTR) | 318-437 | 431 | 12.9 | 9.44 | 16.5 | ND |
| Serum human PCPE | PCPE | 26-446 | 29, 431 | 45.5 | 7.55 | ~51-53 (Lab) | 6.5-7.5 (Lab) |
| | N-terminal fragment (CUB 1 + 2) | 26-300 | 29 | 29.6 | 5.5 | ND | ND |
| | C-terminal fragment (NTR) | 318-437 | 431 | 12.9 | 9.44 | ND | ND | rhPCPE = Recombinant human PCPE
shPCPE = Serum human PCPE
ND = Not Detected
Lab = our laboratory results Further experiments (data not shown) demonstrated that severe caloric restriction of up to 40% in rats and mice, sufficient to significantly reduce growth of the animals, also causes changes in the PCPE isoform pattern, as opposed to animals that were not subject to such caloric restriction. Therefore, PCPE may also be an important diagnostic or prognostic marker for diseases or conditions that affect bone growth. This is also supported by the changes in PCPE patterns seen in children before and after growth hormone treatment, as described above.

All of these results also support the use of PCPE as a clinical biomarker, whether for diagnosis, prognosis, therapy While the invention has been described with respect to a limited number of embodiments, it will be appreciated that many variations, modifications and other applications of the invention may be made.

Sequence Listing

SEQ ID NO: 1
MLPAATASLLGPLLTACALLPFAQGQTPNYTRPVFLCGGDVKGESGYVA

SEGFPNLYPPNKECIWTITVPEGQTVSLSFRVFDLELHPACRYDALEVF

AGSGTSGQRLGRFCGTFRPAPLVAPGNQVTLRMTTDEGTGGRGFLLWYS

```
-continued
GRATSGTEHQFCGGRLEKAQGTLTTPNWPESDYPPGISCSWHIIAPPDQ

VIALTFEKFDLEPDTYCRYDSVSVFNGAVSDDSRRLGKFCGDAVPGSIS

SEGNELLVQFVSDLSVTADGFSASYKTLPRGTAKEGQGPGPKRGTEPKV

KLPPKSQPPEKTEESPSAPDAPTCPKQCRRTGTLQSNFCASSLVVTATV

LKSMVREPGEGLAVTVSLIGAYKTGGDLPSPPTGASLKFYVPCKQCPPM

KKGVSYLLMGQVEENRGPVLPPESFVVLHRPNQDQILTNLSKRKCPSQP

VRAAASQD
```

BIBLIOGRAPHY

01. Gerstenfeld L C, Chipman S D, Kelly C M, Hodgens K J, Lee D D, Landis W J. Collagen expression, ultrastructural assembly, and mineralization in cultures of chicken embryo osteoblasts. J. Cell Biol. 1988 106(3):979-89.
02. Myllyharju J, Kivirikko K I. Collagens and collagen-related diseases. Ann Med. 2001; 33(1):7-21.
03. Myllyharju J, Kivirikko K I. Collagens, modifying enzymes and their mutations in humans, flies and worms. Trends Genet. 2004 20(1):33-43.
04. Hulmes D J. Building collagen molecules, fibrils, and suprafibrillar structures. J Struct Biol. 2002 137(1-2):2-10
05. Stein G S, Lian J B, Owen T A. Relationship of cell growth to the regulation of tissue-specific gene expression during osteoblast differentiation. FASEB J. 1990 (13):3111-23.
06. Prockop D J, Kivirikko K I. Collagens: molecular biology, diseases, and potentials for therapy. Annu Rev Biochem. 1995 64:403-34.
07. Kessler E, Takahara K, Biniaminov L, Brusel M, Greenspan D S. Bone morphogenetic protein-1: the type I procollagen C-proteinase. Science. 1996 271(5247):360-2.
08. Prockop D J, Sieron A L, Li S W. Procollagen N-proteinase and procollagen C-proteinase. Two unusual metalloproteinases that are essential for procollagen processing probably have important roles in development and cell signaling. Matrix Biol. 1998 16(7):399-408.
09. Ge G, Greenspan D S. Developmental roles of the BMP1/TLD metalloproteinases. Birth Defects Res C Embryo Today. 2006 78(1):47-68.
10. Kadler K E, Hojima Y, Prockop D J. Assembly of collagen fibrils de novo by cleavage of the type I pC-collagen with procollagen C-proteinase. Assay of critical concentration demonstrates that collagen self-assembly is a classical example of an entropy-driven process. J Biol. Chem. 1987 262(32):15696-701.
11. Kadler K E, Holmes D F, Trotter J A, Chapman J A. Collagen fibril formation. Biochem J. 1996 316 (Pt 1):1-11.
12. Adar R, Kessler E, Goldberg B. Evidence for a protein that enhances the activity of type I procollagen C-proteinase. Coll Relat Res. 1986 6(3):267-77
13. Kessler E, Adar R. Type I procollagen C-proteinase from mouse fibroblasts. Purification and demonstration of a 55-kDa enhancer glycoprotein. Eur J. Biochem. 1989 186 (1-2):115-21.
14. Yang L, Grey V. Pediatric reference intervals for bone markers. Clin Biochem. 2006 39(6):561-8.
15. Seibel M J. Biochemical markers of bone turnover: part I: biochemistry and variability. Clin Biochem Rev. 2005 26(4):97-122.
16. Gelse K, Poschl E, Aigner T. Collagens—structure, function, and biosynthesis. Adv Drug Deliv Rev. 2003 55(12):1531-46.
17. Voorzanger-Rousselot N, Garnero P. Biochemical markers in oncology. Part I: molecular basis. Part II: clinical uses. Cancer Treat Rev. 2007 33(3):230-83.
18. Wozney J M, Rosen V, Celeste A J, Mitsock L M, Whitters M J, Kriz R W, Hewick R M, Wang E A. Novel regulators of bone formation: molecular clones and activities. Science. 1988 242(4885):1528-34.
19. Gautschi O P, Frey S P, Zellweger R. Bone morphogenetic proteins in clinical applications. ANZ J. Surg. 2007 77(8):626
20. Takahara K, Kessler E, Biniaminov L, Brusel M, Eddy R L, Jani-Sait S, Shows T B, Greenspan DS. Type I procollagen COOH-terminal proteinase enhancer protein: identification, primary structure, and chromosomal localization of the cognate human gene (PCOLCE). J Biol. Chem. 1994 269(42):26280-5.
21. Mott J D, Thomas C L, Rosenbach M T, Takahara K, Greenspan D S, Banda M J. Post-translational proteolytic processing of procollagen C-terminal proteinase enhancer releases a metalloproteinase inhibitor. J Biol. Chem. 2000 275(2):1384-90
22. Steiglitz B M, Keene D R, Greenspan D S. PCOLCE2 encodes a functional procollagen C-proteinase enhancer (PCPE2) that is a collagen-binding protein differing in distribution of expression and post-translational modification from the previously described PCPE1. Biol. Chem. 2002 277(51):49820-30.
23. Moali C, Font B, Ruggiero F, Eichenberger D, Rousselle P, Francois V, Oldberg A, Bruckner-Tuderman L, Hulmes D J. Substrate-specific modulation of a multi-substrate proteinase. C-terminal processing of fibrillar procollagens is the only BMP-1-dependent activity to be enhanced by PCPE-1. J Biol. Chem. 2005 280(25):24188-94.
24. Dumon M F, Nau A, Hervouet M, Paccalin J, Clerc M. Isoelectric focusing (IEF) and immunofixation for determination of disialotransferrin. Clin Biochem. 1996 29(6):549-53.
25. Varki A. Glycan-based interactions involving vertebrate sialic-acid-recognizing proteins. Nature. 2007 446 (7139):1023-9.
26. Pieper R, Gatlin C L, Makusky A J, Russo P S, Schatz C R, Miller S S, Su Q, McGrath A M, Estock M A, Parmar P P, Zhao M, Huang S T, Zhou J, Wang F, Esquer-Blasco R, Anderson N L, Taylor J, Steiner S. The human serum proteome: display of nearly 3700 chromatographically separated protein spots on two-dimensional electrophoresis gels and identification of 325 distinct proteins. Proteomics. 2003 3(7):1345.
27. Sharp M. Bone disease of prematurity. Early Hum Dev. 2007 83(10):653-8.
28. Mundy G R. Metastasis to bone: causes, consequences and therapeutic opportunities. Nat Rev Cancer. 2002 2(8):584-93.
29. Xiao Z, Camalier C E, Nagashima K, Chan K C, Lucas D A, de la Cruz M J, Gignac M, Lockett S, Issaq H J, Veenstra T D, Conrads T P, Beck G R Jr. Analysis of the extracellular matrix vesicle proteome in mineralizing osteoblasts. J Cell Physiol. 2007 210(2):325-35
30. Harris S A, Enger R J, Riggs B L, Spelsberg T C. Development and characterization of a conditionally immortalized human fetal osteoblastic cell line. J Bone Miner Res. 1995 10(2):178-86.
31. Beck G R Jr, Sullivan E C, Moran E, Zerler B. Relationship between alkaline phosphatase levels, osteopontin expression, and mineralization in differentiating MC3T3-E1 osteoblasts. J Cell Biochem. 1998 68(2):269-80.

What is claimed is:

1. A method of analyzing bone formation or determination of cell state with regard to differentiation of osteoblasts and/or fibroblasts in a subject, the method comprising:
   detecting PCPE isoforms in a biological sample from said subject; and
   comparing the glycosylation pattern of said PCPE isoforms from said sample of biological fluid with a glycosylation pattern of PCPE isoforms of a predetermined standard or a sample obtained from healthy individuals, wherein a difference in the glycosylation pattern of PCPE isoforms in the biological sample from the subject relative to the glycosylation pattern of PCPE isoforms in the sample of the predetermined standard or healthy individuals is indicative of a difference in bone formation or cell state relative to the standard or healthy individuals.

2. The method of claim 1, wherein said detecting, further comprises separating PCPE isoforms of the biological sample using a technique selected from the group consisting of electrophoresis separation and chromatography separation, and wherein said electrophoresis separation comprises one or more of SDS-polyacrylamide gel electrophoresis SDS-PAGE), isoelectrofocusing (IEF) and 2 dimensional electrophoresis (2DE), and said chromatography separation comprises one or more of gel filtration, adsorption, ion exchange, and affinity separation.

3. The method of claim 1, wherein said detecting further comprises detecting PCPE isoforms with mass spectroscopy.

4. The method of claim 2, wherein said detecting and said separating are combined in LC-MS/MS (liquid chromatography combined with mass spectroscopy).

5. The method of claim 1, wherein said detecting comprises; contacting the biological sample with anti-PCPE antibody to form a PCPE/anti-PCPE antibody complex; and
   detecting the complex.

6. The method of claim 1, wherein said PCPE is PCPE-1.

7. The method of claim 1, wherein the biological fluid is serum, plasma or blood.

8. The method of claim 1, wherein the PCPE isoforms are differentially present between a biological sample from a subject and a predetermined sample or a sample obtained from healthy individuals and are used as a clinical biomarker for determination of normal bone growth or for diagnosis, prognosis, therapy selection or a clinical endpoint marker for a disease selected from the group consisting of:

(i) a disease due to regulation of fibrillar collagen synthesis, such as organ fibrosis, genetic fibrosis, idiopathic fibrosis, cardiac fibrosis, arterial blockages and/or fibrosis;

(ii) a bone disease, such as growth disorders, bone disease of premature babies, bone disease of aging, osteoporosis, bone cancer metastasis, Paget's disease, Osteomalacia, Rickets, bone tumors, osteoporosis, lymphoma, leukemia, granular lymphocytic leukemia in the bone marrow and Sezary syndrome; and (iii) bone changes occurring due to parathyroid disorders.

9. The method of claim 8, wherein said growth disorder is genetic or due to malnutrition.

10. The method of claim 8, wherein said bone disease comprises one or more of metastasis of cancer cells to bone or out of bone.

11. The method of claim 8, wherein said organ fibrosis comprises one or more of fibrosis of the liver, lung, heart.

12. The method of claim 1, wherein the PCPE glycosvlation pattern is determined for measuring normal bone growth.

13. The method of claim 1, wherein the PCPE glycosvlation pattern comprises a plurality of different isoforms.

* * * * *

SEQUENCE LISTING

<160> NUMBER OF SEQ ID NOS: 1

<210> SEQ ID NO 1
<211> LENGTH: 449
<212> TYPE: PRT
<213> ORGANISM: Homo sapiens

<400> SEQUENCE: 1

Met Leu Pro Ala Ala Thr Ala Ser Leu Leu Gly Pro Leu Leu Thr Ala
1               5                   10                  15

Cys Ala Leu Leu Pro Phe Ala Gln Gly Gln Thr Pro Asn Tyr Thr Arg
            20                  25                  30

Pro Val Phe Leu Cys Gly Gly Asp Val Lys Gly Glu Ser Gly Tyr Val
        35                  40                  45

Ala Ser Glu Gly Phe Pro Asn Leu Tyr Pro Pro Asn Lys Glu Cys Ile
    50                  55                  60

Trp Thr Ile Thr Val Pro Glu Gly Gln Thr Val Ser Leu Ser Phe Arg
65                  70                  75                  80

Val Phe Asp Leu Glu Leu His Pro Ala Cys Arg Tyr Asp Ala Leu Glu
                85                  90                  95

Val Phe Ala Gly Ser Gly Thr Ser Gly Gln Arg Leu Gly Arg Phe Cys
            100                 105                 110

Gly Thr Phe Arg Pro Ala Pro Leu Val Ala Pro Gly Asn Gln Val Thr
        115                 120                 125

Leu Arg Met Thr Thr Asp Glu Gly Thr Gly Gly Arg Gly Phe Leu Leu
    130                 135                 140

Trp Tyr Ser Gly Arg Ala Thr Ser Gly Thr Glu His Gln Phe Cys Gly
145                 150                 155                 160

Gly Arg Leu Glu Lys Ala Gln Gly Thr Leu Thr Thr Pro Asn Trp Pro
                165                 170                 175

Glu Ser Asp Tyr Pro Pro Gly Ile Ser Cys Ser Trp His Ile Ile Ala
            180                 185                 190

Pro Pro Asp Gln Val Ile Ala Leu Thr Phe Glu Lys Phe Asp Leu Glu
        195                 200                 205

Pro Asp Thr Tyr Cys Arg Tyr Asp Ser Val Ser Val Phe Asn Gly Ala
    210                 215                 220

Val Ser Asp Asp Ser Arg Arg Leu Gly Lys Phe Cys Gly Asp Ala Val
225                 230                 235                 240

Pro Gly Ser Ile Ser Ser Glu Gly Asn Glu Leu Leu Val Gln Phe Val
                245                 250                 255

Ser Asp Leu Ser Val Thr Ala Asp Gly Phe Ser Ala Ser Tyr Lys Thr
            260                 265                 270

Leu Pro Arg Gly Thr Ala Lys Glu Gly Gln Gly Pro Gly Pro Lys Arg
        275                 280                 285

Gly Thr Glu Pro Lys Val Lys Leu Pro Pro Lys Ser Gln Pro Pro Glu
    290                 295                 300

Lys Thr Glu Glu Ser Pro Ser Ala Pro Asp Ala Pro Thr Cys Pro Lys
305                 310                 315                 320

Gln Cys Arg Arg Thr Gly Thr Leu Gln Ser Asn Phe Cys Ala Ser Ser
                325                 330                 335

Leu Val Val Thr Ala Thr Val Lys Ser Met Val Arg Glu Pro Gly Glu
            340                 345                 350

Gly Leu Ala Val Thr Val Ser Leu Ile Gly Ala Tyr Lys Thr Gly Gly
        355                 360                 365

-continued

```
Leu Asp Leu Pro Ser Pro Pro Thr Gly Ala Ser Leu Lys Phe Tyr Val
    370             375             380

Pro Cys Lys Gln Cys Pro Pro Met Lys Lys Gly Val Ser Tyr Leu Leu
385             390             395                         400

Met Gly Gln Val Glu Glu Asn Arg Gly Pro Val Leu Pro Pro Glu Ser
                405             410                 415

Phe Val Val Leu His Arg Pro Asn Gln Asp Gln Ile Leu Thr Asn Leu
            420             425             430

Ser Lys Arg Lys Cys Pro Ser Gln Pro Val Arg Ala Ala Ala Ser Gln
        435             440             445

Asp
```